(12) United States Patent
Kochian et al.

(10) Patent No.: US 7,582,809 B2
(45) Date of Patent: Sep. 1, 2009

(54) SORGHUM ALUMINUM TOLERANCE GENE, SBMATE

(75) Inventors: Leon Kochian, Ithaca, NY (US); Jiping Liu, Ithaca, NY (US); Jurandir Vieira de Magalhaes, Belo Horizonte-MG (BR); Claudia Teixeira Guimaraes, Sete Lagoas-MG (BR); Robert Eugene Schaffert, Sete Lagoas-MG (BR); Vera Maria Carvalho Alves, Sete Lagoas-MG (BR); Patricia Klein, College Station, TX (US)

(73) Assignees: The United States of America as represented by the Secretary of Agriculture, Washington, DC (US); Empresa Brasileira de Pesquisa Agropecuaria, Embrapa (BR)

( * ) Notice: Subject to any disclaimer, the term of this patent is extended or adjusted under 35 U.S.C. 154(b) by 0 days.

(21) Appl. No.: 11/804,164

(22) Filed: May 17, 2007

(65) Prior Publication Data

US 2008/0289062 A1    Nov. 20, 2008

(51) Int. Cl.
*A01H 5/00* (2006.01)
*C12N 15/82* (2006.01)
*C12N 15/63* (2006.01)
*C07H 21/04* (2006.01)

(52) U.S. Cl. .................. 800/295; 800/278; 435/243; 435/320.1; 435/468; 536/23.1; 536/23.6

(58) Field of Classification Search .............. None
See application file for complete search history.

(56) References Cited

OTHER PUBLICATIONS

Wells (Biochemistry 29:8509-8517, 1990).*
Ngo et al., (The Protein Folding Problem and Tertiary Structure Prediction, K. Merz., and S. Le Grand (eds.) pp. 492-495, 1994).*
Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*

* cited by examiner

*Primary Examiner*—Phuong T Bui
*Assistant Examiner*—Vinod Kumar
(74) *Attorney, Agent, or Firm*—John D. Fado; Evelyn M. Rabin

(57) ABSTRACT

The major aluminum tolerance gene, the SbMATE gene, encodes a root citrate efflux transporter that is Al-inducible at the level of gene transcription and is also Al-activated at the level of protein function. High level of expression of the SbMATE gene and the protein was found in roots. SbMATE orthologs with high degree of sequence homology were found in other higher plants, including rice. Successful transformation of *Arabidopsis* provides strong evidence that SbMATE can work across species to enhance tolerance to Al in other important crops grown in localities worldwide where $Al^{3+}$ cations are present in acid soils and are toxic to plants.

29 Claims, 12 Drawing Sheets
(3 of 12 Drawing Sheet(s) Filed in Color)

a b c

LD of significant SNPs and Indels

SEQUENCE LISTING

<160> NUMBER OF SEQ ID NOS: 34

<210> SEQ ID NO 1
<211> LENGTH: 10690
<212> TYPE: DNA
<213> ORGANISM: Sorghum bicolor

<400> SEQUENCE: 1

```
acatctcatg aagagcaacc cggaattgaa gtttgacact gaatttggca cccaccatga      60
tttagatccc tgcatgagag acaagagaga atctttctgg ttaccacaca gttttgttaa     120
gattgtattc ttcattgatt attgatagag aaagaagaga tagatgatga gtgtaccctt     180
gaagtggctg cacatgctgc tgtaatatca gttatccttt ggtatgaata aatataagtt     240
ccgtacccaa aacatactga cataataata actgcactaa caaggaaatc tatgagtgtc     300
ctcattattt gtgcatgcct cgtgtcctgc atctgagtct tgaatttctc cgtttggaag     360
gaagctttct gaaatcccaa ggataactta atcttgtcta acatgtgcga gtaggagtta     420
agttctagtt gagactgttt aagttgcaac tttctcatgc taaggcttat ctcaaattcc     480
ttgagctcat ttgaccgagt ttgttctttc aaagatcttt caaatgcatt aaggatccgc     540
cgattagctt caggagaaga tatgctatga gtacgacgag tcagctgctg attgccacca     600
gcatacagaa caagctgact ttccactgaa tttgaaaggt cctgcttgat ttcttgcgtt     660
ggattttgtg gaccatcagt gctcaacttg cttgcagcat cagagtcttc atgcttagaa     720
gaacattgag gaactggacc ttgtccatag acaggcatct cattaacaag atgaagcgtt     780
gttaatgtgc tgctgaatga tttctcaaag tttctcataa aactgtctaa cttgttacca     840
tatatctaca atgatgagtg aaagatatat taggaataat attaacaact gagctgtggg     900
atgataaagg gaactaggct tacatttctc aatgattcct tcactgccga tgtacagatc     960
tgcatccaaa gtccagactc agtttcaaac tacaaacagt ttcgtggttt tgtagagttt    1020
attagtcaaa ttgtggtaca ataaccttgg aaagaagtgc aggctgtatt ctttcgcctg    1080
aaggattctt cgtattcaca acctgcaatc agcaaatgca actcattgcc ctgaacagaa    1140
acttaggtgc acaaaaaaca tggcatgtga tgatgctaac atgaagttgc atgttggtga    1200
aatataggat tgtctactgg tgttctcatg tgaatgatga tgcctctgga tacacactga    1260
ggtgtgggca gacaatcata tgaaatgtaa tctcatgctt aatttcggaa tggatagcaa    1320
tgtgcaatac aagatgaaca aaactcttgt acgcccccac agaaatggaa taaagtgaca    1380
atttccctcc cccccaaagg gtactcctca cttgtatggc tctatcacca cttctctgac    1440
cccaagctgc acatttgac atgtgatgca cgattgctcg gaataattgc aatttgcaac    1500
gacaaacgaa acgaaaatga tccagggcgg cggtatttag cattgcgcgc ccgcctccta    1560
tcctatctgt ggactagcaa ccaaggctac agacttacgt acaattcggt agaacggtga    1620
agggtgaaat gcggacatca acaccggtcg gcccgtcgtt accaacccgc gccagaaatg    1680
ggggaagcta cagagaaagg ccgagggagt ggcagtgggt acacgcacct gcgcgaggac    1740
ggccgcgaac gacatcccga gaggcagcgc gaggtcgtcc tgcacctgcg cgccggcgcc    1800
accctgaccc tcgctcccgc ccgcgggcgt agcggcgggc ccggctcct gccgccttcg    1860
ccgcagccgc agccggagcc ggacacccct gctgcgccga gcggaggagg accggaggc    1920
agaggcggat gctgagccgc atgccgagga ggcgtctccc gacgcctccg acgaggaggg    1980
gtcggcgggt gcgggtgggt ggaggcagcc cgtgtccatc tcggcggggc cggcggggca    2040
```

```
ggggacaggg cgaccgttct gggctctggg gtgttccttt cttcaggcca gggccaggga   2100
cctagggctg cgctgtctgt gtgtgatttg gttccgtttt gacttcgctt tggaaggaga   2160
gggacggacg gggacgccgt cggaacgggt gggcggagtg tcccagtcga agcgcccgtg   2220
ggaacgcgag aaatgaagtt attattacag gaggcgggat tagccgtttg aagtgaaaat   2280
cctgggaaag ttattaattc cataatttgt ttcggaaaat tcgattttt attaaaaaat    2340 gagtttaggg agccgacagc cgaggtcgga gactctggtc cggagcggcg caacggcacg   2400
tctgattgcc gacgtggggc ccagcggccc agcaaaggcc ggtccgggcc gtactatttt   2460
gaagtccaaa tataagaagg cttgggctgt cagcccagga cagaacgtac ttttccgaag   2520
cccaagatat aagaaggatt gagctgtcat gtaaagaacg acttacaaaa aaaattacaa   2580
tatcattttc taaaaaaaat tacaatatca tagggtagga aatatggata ggacatagga   2640
ggtgtgggta tcgcgttccc atgtacctct cgcaagctaa gcgaaaatgt gcttgtgcta   2700
acagctacat atatatagct gaatttccca caaaaaaaaa gctatatata gctgaaacag   2760
cagtttgtta tgacatattt tggagcacac agtcgtggag caatttatt tttcaacctt    2820 ttatagctat atactatttt aaaataacat gtaagaatag aactagcctt ttggttgtgt   2880
cagactgcca tgcatagaaa aaattataat gtcatatgca ttgggcacaa ctgcacaaag   2940
gcatggtatg ctaaagctct acccctcaat caaaaaataa taaaattcta gcacagtacc   3000
tagtatctgg attttgaata gctatatata taaaaacact aatatttatt atatcaaata   3060
cttcctccat cccaaaagca ttcaaagttt atcataaaat tgttatcatt cttactttcc   3120
aatgcatatt tatttttca taatacaccc ttttttcaa tacatctcta tctttatt      3180 ctctctatct ctcttctttt ttgtgcatta taacttttca ttgtttctta atttccatat   3240
ttatatgctt ttgtaatgga gggagcaagt gttatcatta gatttattta tgaattatat   3300
ttgtacggta tatctatttg gtgttagacg ttgttatcgt atctatgtat ttagtcaaat   3360
tttagatatt tcaactatag atgcacctat aatcttgttt ttcagaacac acctagaatt   3420
ataatttttt ttaggacaga catactccct ttgtcccaaa ataaacgtat gcctcacgtt   3480
tcgagaagtt atttttttta aagtcttact agttatataa aagatcatat taatatttgt   3540
attttgaaat aagcttgcta tgaaaatata ttatatgacc aatgtagtga tgcttattat   3600
tacacactat agatatcagt acttttgtat atatatttgg ttaaacataa aaaaaagctt   3660
aactctttga taaacgataa aagttgtgtg tattttgggg ccgacgatga agtaatatat   3720
ttttatttca tgctgccggc gcgtatttg cacaccgcct tttcagtttt tacgcatttt     3780
ctctgtagta gtatatgaca acaattccta ggatccagtg agctaccggt gaaggtgctc   3840
gttatgcgtt taaacattgt tccgtccggc ggcatctagc taggagtact cctacagact   3900
attaaagttg ggccttgttt agttccaaat aattttgcaa aataggaata gtagcatttt   3960
cgtttgtatt tgacaaatat tgtccaatca tgaactaatt agactcaaaa gattcgtctc   4020
gttaatttcg accaaactgt gaaattagtt tttattttcg tctatattta atacttcatg   4080
catgcgtcta aagatttgat gtgacggaga atctaaaaaa ttttgcaaaa cttttgggga   4140
actaaacaag gccttggttg gtgcgatgat gttggatcca gtgagctacc ggtgaaggtg   4200
ctcgttatgc gtttaaacat tgttccgtcc ggcggcatct agctaggagt actcctacag   4260
actattaaag ttgggccttg tttagttcca ataattttg caaaataggaata gtagcat    4320 tttcgtttgt atttgacaaa tattgtccaa tcatgaacta attagactca aaagattcgt   4380
```

```
ctcgttaatt tcgaccaaac tgtgaaatta gtttttattt tcgtctatat ttaatacttc   4440
atgcatgcgt ctaaagattt gatgtgacgg agaatctaaa aaattttgca aaacttttg    4500 ggaactaaac aaggccttgg ttggtgcgat gatgttggat ccagtgagct accggtgaag   4560
gtgctcgtta tgcgtttaaa cattgttccg tccggcggca tctagctagg agtactccta   4620
cagactatta aagttgggcc ttgtttagtt ccaaataatt ttgcaaaata ggaatagtag   4680
cattttcgtt tgtatttgac aaatattgtc caatcatgaa ctaattagac tcaaaagatt   4740
cgtctcgtta atttcgacca aactgtgaaa ttagttttta ttttcgtcta tatttaatac   4800
ttcatgcatg cgtctaaaga tttgatgtga cggagaatct aaaaaatttt gcaaaacttt   4860
ttgggaacta acaaggcct tggttggtgc gatgatgttg gatccagtga gctaccggtg    4920
aaggtgctcg ttatgcgttt aaacattgtt ccgtccggcg catctagct aggagtactc    4980 ctacagacta ttaaagttgg gccttgttta gttccaaata ttttgcaaa ataggaatag    5040 tagcattttc gtttgtattt gacaaatatt gtccaatcat gaactaatta gactcaaaag   5100
attcgtctcg ttaatttcga ccaaactgtg aaattagttt tattttcgt ctatatttaa    5160 tacttcatgc atgcgtctaa agatttgatg tgacggagaa tctaaaaaat tttgcaaaac   5220
tttttgggaa ctaaacaagg ccttggttgg tgcgatgatg ttggatccag tgagctaccg   5280
gtgaaggtgc tcgttatgcg tttaaacatt gttccgtccg gcggcatcta gctaggagta   5340
ctcctacaga ctattaaagt tgggccttgt ttagttccaa ataattttgc aaaataggaa   5400
tagtagcatt ttcgtttgta tttgacaaat attgtccaat catgaactaa ttagactcaa   5460
aagattcgtc tcgttaattt cgaccaaact gtgaaattag ttttatttt cgtctatatt    5520 taatacttca tgcatgcgtc taaagatttg atgtgacgga gaatctaaaa aattttgcaa   5580
aactttttgg gaactaaaca aggccttggt tggtgcgatg atgttggatc cagtgagcta   5640
ccggtgaagg tgctcgttat gcgtttaaac attgttccgt ccggcggcat ctatactcct   5700
acagactatt aaagttggtt ggcgtttgct gctttattaa tgcatgcatc aagcatgggg   5760
ccatcaacgg cagtgtcact tgactcaatg accaaacacc aaagcatgcc tggttaattt   5820
cagttaataa gagggccttc aaaggcagtc tcactcagga cagtgttttt atgtcactgt   5880
tttcggatta gctaaaaagt atttgtactg agataaaaat attgtagaat gactgataaa   5940
tttggctgga tgcatatgca taaacacgtg tcacgaatcc atattggatg cacatggtta   6000
ctccatagag tggcctttgt taacgcgcgc ctgttgtgtc acagatttat aagctagcta   6060
tagtatttta attcttctat ggtattattg taagcaaata tgtcgtatga agttgttaac   6120
taggaaactg aggcccgcct taagttccag tgttcattca cgaataatga attaatatct   6180
tgagcaaaaa gataataaca atgttaggcc aaagtgttgg gtgaaactaa aatcgaacta   6240
gcataatact gtacagtaat tcagttgttt cctttaaat ataaataaaa tcaagcctga    6300
gtgccacaac tctatggagc actccatctg ttcttttata tttgtcgtca cgtcgaccaa   6360
actttctcat ttttaactaa gtttatataa aagattaaca atatttgtat ctctaaataa   6420
atttacataa aaatagattc agtgatctct aattatatat actaattacg tgtcacaaat   6480
attaatattt tttatatatt taatcaaagt taattacgtc aaatgaaatg atcagtgccc   6540
ggcagttcca taccacactt tcacggcacc acttcctccg aacaaaacgt atcctaaaaa   6600
aagaaaaaat cctttggatt ctgtctctct tagcttaaat atcctcgact tgacagtgtt   6660 tgcatttct tgtttttct ctaagatttg atgatgttgt tatttagta gtataagcga     6720 catgcccttt gacaatgagg cgtccatggt agatttctat caatttcaaa atttgttgga   6780
```

```
ctctagctca atgttttcga aatgctcgta gaggtaaagt gtttatatgt atgttcacgt    6840
gagcctgcat ctttaacgtg atttgaaaga agaaaaaacc ttcgtcatgt ggctcatcat    6900
cagggttcaa gtactacctt gctttagttt tgattgttgt ggaggttaat gactaattta    6960
gaggtgttaa catgtctttc taaaaacttg caaagttaga aatgttaatt tagtagcaag    7020
cacacacccc aaactcttcc ctctccatgt ggctagctgg gctggaggct gcctgcctgc    7080
ctatataagg atgggttgct cggccacttg tcacacccac tccatcacca gttcaccact    7140
cgtccgcttc accaacctat agagtttatg ccccgtcttg ctcttcagct ctggttagtc    7200
attaagagtc tgtttagatc tcaaattttt acatctcaaa acttttggct ctaaagttta    7260
catttcaaat aggtgttttg atgctttcca aattttctg gtctgcaaca cacaagacac      7320 ggcccctaa gcaagtttac acagtttgag ggctccaagg tccaaaattc caaatcttta     7380
caacctaagt gttacaggcc ctctttagat ccattcttct aaaagtgcc catttttcca      7440 aaagttttgg ctgtttagct gcatctggcg taattatcct gttatttat tcctctatga      7500 tgatgtagga gcatatatta ctgcacaagt ccttgttaat taatttgaga cagtcaggta    7560
ttagagggta gtagtagaac aacaagtggc caagtgggtg atcataagtc agttgttttt    7620
ttcttgaaaa tgctgttgtt atcactgatc gaatggttaa tgtgccgtat tgtagtgctt    7680
gcaaggtttg tagctaggcc gacatggagg aacaccggtc accagctcac gccaagcccg    7740
aggccgagca gccaccgcag cagcaggtgc cggcggcgat ggcggtggca gtggcagtgg    7800
acgtcgctgc tccagcagcg ctacagaata gtactgcggc tcctgctgag aacggggacg    7860
tcgctgctgc gggcgcggca gagaatggta ctgcggcttc cgctgcgaac ggggacggcg    7920
gcggctcgga gctgctcggc ggtccacgct ggacggggct gcaccttttc gtgatgaaca    7980
tccggagcgt gttcaagctg gacgagctcg gcgcggaggt gctgggcatc gcggtgccgg    8040
cgtcgctggc gctgacggcc gacccgctcg cctcgctgat cgacacggcc ttcatcggcc    8100
ggctggggtc cgtggagatc gcggccgtgg gcgtcgccat cgcggtgttc aaccaggtca    8160
tgaaggtgtg catctacccg ctcgtcagcg tcaccacgtc gttcgtcgcg gaggaggacg    8220
ccgtgctcag caaaggcggc gccaaggtca tcgacaacgg agaagaagaa gaagaattag    8280
aagcgggaca agttggcccg gagaagcaca ctgccgctgc cggcgcggac ccggagaagc    8340
agcagcagcc agctgatgaa gaagccgcca agaacggcgg cgagggatgc gcccctgccg    8400
tcgtcgccgg ccggagtagc ggcaagaaat cagggaacag gaggttcgtg ccgtccgtga    8460
cgtcggcact gatcgtgggc gcgctcctgg ggctgttcca gaccgtcttc ctcgtcgccg    8520
ccggaaagcc gctgctgcgc ctcatgggcg tcaagccggt aagttactgt gcctgtgcgt    8580
gcccgcaccg catgcaacgg tgaactagat tcgtcggtgc aacgacgaac aattgcttat    8640
acaatttact ggtgatattc gaatgatttc ccagggttcg cccatggtga tgcccgcgct    8700
gcgctacctg acgctgcgcg cgcttggcgc cccggccgtg ctgctgtctc tcgccatgca    8760
aggagtcttc cgtgggttca aggacgccaa gacgccctta tacgccatcg gtaaccaata    8820
atgctccata catgatacat acaatgcggc catatatgtc aaccaggcaa accagcatgg    8880
ttttttcggt aaagtttatt ttgcccttga ggacatgtgt ccttactctc tcatccattg    8940
gattcgcttt aagaaatgtg caaacacaca tctcaaagcg aaactacttt gatatgtatg    9000
tttgcacact tctcaaaacg aatctaatgg gtgggagagt gagagtatat gcccttaacg    9060
gaaaaaaaaa cacccacgca cgtttgatct gagctgtgtt acgaatgaat gcatgcagtg    9120
```

-continued

```
gccggcgacg cggcgaacat tgtgctggat ccgatcctga tatttggctg ccgcctgggc   9180
gtgatcggcg cagccattgc ccatgttctt tcccagtata agaccatgac cacccatctc   9240
cttcttgtca gcaattcagc attggccgca caactgaca atggcgaaat taaaccgcac   9300
gtacgcaggt acctgataac gctgataatg ctgagcaagc tggtgaggaa ggtcgatgtc   9360
gtcccgccca gcctgaaatg cctcaaattc cggcgcttcc tcggatgcgg tcagtagtcg   9420
atcagtagga tttggatcca ttaacaagac gagatgatga cgaggttata atattgaccc   9480
tgtatatgtg tgtataggat tccttctgct ggcacgggtg gtggccgtga cgttctgcgt   9540
gacgctggcg gcgtcgctgg ctgctcgcca cgggccgacc gccatggccg ccttccagat   9600
ctgcacccag gtctggctgg ccacgtccct cctcgccgac gggctcgccg tcgccggcca   9660
ggccatgatc gcgagcgcct cgccaagga ggaccgctac aaggtggccg ccaccgccgc   9720
gcgcgtcctg cagctcggcg tcgtcctggg cgccgccctc acggcgctcc tcggactcgg   9780
gctgcagttc ggagccggcg tcttcaccag cgacgccgcc gtcatcaaga ccatccggaa   9840
gggcgttccg ttcgtcgccg gcacgcagac gctcaacacg ctagccttcg tcttcgacgg   9900
catcaacttc ggcgcgtcgg actacgcctt ctctgcctac tccatgatcg gcgtggcggc   9960
tgtcagcatc ccgtcgctca tcttcctctc gtcgcacggc ggcttcgtcg gcatctgggt  10020
agccctcacc atctcacatgg gcgtcagggc ccttgccagc acctggagga tggcagcagc  10080
ccaggggcca tggaagtttc ttcggcagtg agcatatacg tacagtctcg tgtcgatcgt  10140
actttacctt gattttagtt ttatttctta tttgtaaccg aaggatactg gctacttgca  10200
aagcctaaat gttctaatgt aactagaaac aaatagtcat gatgaaaaca atatggttag  10260
catttctagc aacgctattt acacgagtca tcttgtttga ttttttttaa taaataattt  10320
taagaaagaa gtgagtatat gagttacaca ataacacgca caacccaaac gaccctagta  10380
cgtagagatt ggaatgaatc caagaataga cttacacaca agaccagctg gtgccgtcac  10440
atgcgtctga tcgaaaacaa gattaatcaa agaaagaaa aaacaccgaa gccagcaatg  10500
caacacaagc acagatcaag aaagaaacag gggactttga cagccacgcg gcagcaacta  10560
atacgccgat cgagctccgg ccgacgttgt cccacggtcg tcgtcgtcgt cgatcgcatg  10620
tagatatagt agtacggtaa cgctgcgtgg tgagaggcga ggcatgtggc cggcaggcag  10680
gcatgggttg                                                          10690
```

<210> SEQ ID NO 2
<211> LENGTH: 9979
<212> TYPE: DNA
<213> ORGANISM: Sorghum bicolor

<400> SEQUENCE: 2

```
acatctcatg aagagcaacc cggaattgaa gtttgacact gaatttggca cccaccatga     60
tttagatccc tgcatgagag acaagagaga atctttctgg ttaccacaca gttttgttaa    120
gattgtattc ttcattgatt attgatagag aaagaagaga tagatgatga gtgtaccctt    180
gaagtggctg cacatgctgc tgtaatatca gttatccttt ggtatgaata aatataagtt    240
ccgtacccaa aacatactga cataataata actgcactaa caaggaaatc tatgagtgtc    300
ctcattattt gtgcatgcct cgtgtcctgc atctgagtct tgaatttctc cgtttggaag    360
gaagctttct gaaatcccaa ggataactta atcttgtcta acatgtgcga gtaggagtta    420
agttctagtt gagactgttt aagttgcaac tttctcatgc taaggcttat ctcaaattcc    480
ttgagctcat ttgaccgagt tgttctttc aaagatcttt caaatgcatt aaggatccgc    540
```

```
cgattagctt caggagaaga tatgctatga gtacgacgag tcagctgctg attgccacca      600
gcatacagaa caagctgact ttccactgaa tttgaaaggt cctgcttgat ttcttgcgtt      660
ggattttgtg gaccatcagt gctcaacttg cttgcagcat cagagtcttc atgcttagaa      720
gaacattgag gaactggacc ttgtccatag acaggcatct cattaacaag atgaagcgtt      780
gttaatgtgc tgctgaatga tttctcaaag tttctcataa aactgtctaa cttgttacca      840
tatatctaca atgatgagtg aaagatatat taggaataat attaacaact gagctgtggg      900
atgataaagg gaactaggct tacatttctc aatgattcct tcactgccga tgtacagatc      960
tgcatccaaa gtccagactc agtttcaaac tacaaacagt ttcgtggttt tgtagagttt     1020
attagtcaaa ttgtggtaca ataaccttgg aaagaagtgc aggctgtatt ctttcgcctg     1080
aaggattctt cgtattcaca acctgcaatc agcaaatgca actcattgcc ctgaacagaa     1140
acttaggtgc acaaaaaaca tggcatgtga tgatgctaac atgaagttgc atgttggtga     1200
aatataggat tgtctactgg tgttctcatg tgaatgatga tgcctctgga tacacactga     1260
ggtgtgggca gacaatcata tgaaatgtaa tctcatgctt aatttcggaa tggatagcaa     1320
tgtgcaatac aagatgaaca aaactcttgt acgcccccac agaaatggaa taaagtgaca     1380
atttccctcc cccccaaagg gtactcctca cttgtatggc tctatcacca cttctctgac     1440
cccaagctgc cacatttgac atgtgatgca cgattgctcg gaataattgc aatttgcaac     1500
gacaaacgaa acgaaaatga tccagggcgg cggtatttag cattgcgcgc ccgcctccta     1560
tcctatctgt ggactagcaa ccaaggctac agacttacgt acaattcggt agaacggtga     1620
agggtgaaat gcggacatca acaccggtcg gcccgtcgtt accaacccgc gccagaaatg     1680
ggggaagcta cagagaaagg ccgagggagt ggcagtgggg cacgcacct  gcgcgaggac     1740
ggccgcgaac gacatcccga gaggcagcgc gaggtcgtcc tgcacctgcg cgccggcgcc     1800
accctgaccc tcgctcccgc ccgcgggcgt agcggcgggc cccggctcct gccgccttcg     1860
ccgcagccgc agccggagcc ggacacccct gctgcgccga gcggaggagg accgggaggc     1920
agaggcggat gctgagccgc atgccgagga ggcgtctccc gacgcctccg acgaggaggg     1980
gtcggcgggt gcgggtgggt ggaggcagcc cgtgtccatc tcggcggggc cggcggggca     2040
ggggacaggg cgaccgttct ggggtgttcc tttcttcagg ccaggccag  ggacccaggg     2100
ctgcgctgtc tgtgtgtgat ttggttccgt tttgacttcg ctttggaagg agagggacgg     2160
acggggacgc cgtcggaacg ggtgggcgga gtgtcccagt cgaagcgccc gtgggaacgc     2220
gagaaatgaa gttattatta caggaggcgg gattagccgt ttgaagtgaa aatcctggga     2280
aagttattaa ttccataatt tgtttcggaa aattcgattt tttattaaaa aatgagttta     2340
gggagccgac agccgaggtc ggagactctg gtccggagcg gcgcaacggc acgtctgatt     2400
gccgacgtgg ggcccagcgg cccagcaaag gccggtccgg gccgtactat tttgaagtcc     2460
aaatataaga aggcttgggc tgtcagccca ggacagaacg tacttttccg aagcccaaga     2520
tataagaagg attgagctgt catgtaaaga acgacttaca aaaaaaatta caatatcatt     2580
ttctaaaaaa aattacaata tcatagggta ggaaatatgg ataggacata ggaggtgtgg     2640
gtatcgcgtt cccatgtacc tctcgcaagc taagcgaaaa tgtgcttgtg ctaacagcta     2700
catatatata gctgaatttc ccacaaaaaa aaagctatat atagctgaaa cagcagtttg     2760
ttatgacata ttttggagca cacagtcgtg gagcaattta ttttttcaac cttttatagc     2820
tatatactat tttaaaataa catgtaagaa tagaactagc cttttggttg tgtcagactg     2880
```

```
ccatgcatag aaaaaattat aatgtcatat gcattgggca caactgcaca aaggcatggt   2940
atgctaaagc tctacccctc aatcaaaaaa taataaaatt ctagcacagt acctagtatc   3000
tggattttga atagctatat atataaaaac actaatattt attatatcaa atacttcctc   3060
catcccaaaa gcattcaaag tttatcataa aattgttatc attcttactt tccaatgcat   3120
attttatttt tcataataca ccctttttt caatacatct ctatcttta tttctctcta    3180 tctctcttct tttttgtgca ttataacttt tcattgtttc ttaatttcca tatttatatg   3240
cttttgtaat ggagggagca agtgttatca ttagatttat ttatgaatta tatttgtacg   3300
gtatatctat ttggtgttag acgttgttat cgtatctatg tatttagtca aattttagat   3360
atttcaacta tagatgcacc tataatcttg ttttcagaa cacacctaga attataattt    3420
tttttaggac agacatactc cctttgtccc aaaataaacg tatgcctcac gtttcgagaa   3480
gttatttttt ttaaagtctt actagttata taaaagatca tattaatatt tgtattttga   3540
aataagcttg ctatgaaaat atattatatg accaatgtag tgatgcttat tattacacac   3600
tatagatatc agtactttg tatatatatt tggttaaaca taaaaaaag cttaactctt     3660 tgataaacga taaagttgt gtgtattttg gggccgacga tgaagtaata tatttttatt    3720
tcatgctgcc ggcgcgtatt ttgcacaccg ccttttcagt ttttacgcat tttctctgta   3780
gtagtatatg acaacaattc ctaggatcca gtgagctacc ggtgaaggtg ctcgttatgc   3840
gtttaaacat tgttccgtcc ggcggcatct agctaggagt actcctacag actattaaag   3900
ttgggccttg tttagttcca ataattttg caaaatagga atagtagcat tttcgtttgt    3960
atttgacaaa tattgtccaa tcatgaacta attagactca aaagattcgt ctcgttaatt   4020
tcgaccaaac tgtgaaatta gttttattt tcgtctatat ttaatacttc atgcatgcgt    4080
ctaaagattt gatgtgacgg agaatctaaa aaattttgca aaacttttg ggaactaaac    4140 aaggccttgg ttggtgcgat gatgttggat ccagtgagct accggtgaag gtgctcgtta   4200
tgcgtttaaa cattgttccg tccggcggca tctagctagg agtactccta cagactatta   4260 aagtgggcc ttgtttagtt ccaaataatt ttgcaaaata ggaatagtag cattttcgtt    4320
tgtatttgac aaatattgtc caatcatgaa ctaattagac tcaaaagatt cgtctcgtta   4380
atttcgacca aactgtgaaa ttagttttta ttttcgtcta tatttaatac ttcatgcatg   4440
cgtctaaaga tttgatgtga cggagaatct aaaaaatttt gcaaacttt tgggaacta     4500 aacaaggcct tggttggtgc gatgatgttg gatccagtga gctaccggtg aaggtgctcg   4560
ttatgcgttt aaacattgtt ccgtccggcg catctagct aggagtactc ctacagacta    4620
ttaaagttgg gccttgttta gttccaaata ttttgcaaa ataggaatag tagcattttc    4680
gtttgtattt gacaaatatt gtccaatcat gaactaatta gactcaaaag attcgtctcg   4740
ttaatttcga ccaaactgtg aaattagttt ttattttcgt ctatatttaa tacttcatgc   4800
atgcgtctaa agatttgatg tgacggagaa tctaaaaaat tttgcaaaac tttttgggaa   4860
ctaaacaagg ccttggttgg tgcgatgatg ttggatccag tgagctaccg gtgaaggtgc   4920
tcgttatgcg tttaaacatt gttccgtccg gcggcatcta tactcctaca gactattaaa   4980
gttggttggc gtttgctgct ttattaatgc atgcatcaag catgggccca tcaacggtag   5040
tgtcacttga ctcaatgacc aaacaccaaa gcatgcctgg ttaatttcag ttaataagag   5100
ggccttcaaa ggcagtctca ctcaggacag tgtttttatg tcactgtttt cggattagct   5160
aaaaagttat gactaaaagt attattcgct atttgtactg agataaaaat attgtagaat   5220
gactgataaa tttggctgga tgcatatgca taaacacgtg tcacgaatcc atattggatg   5280
```

```
cacatggtta ctccatagag tggcctttgt taacgcgcgg ctgttgtgtc acagatttat   5340
aagctagcta tagtatttta attcttctat ggtattattg taagcaaata tgtcgtatga   5400
agttgttaac taggaaactg aggcccgcct taagttccag tgttcattca cgaataatga   5460
attaatatct tgagcaaaaa gataataaca atgttaggcc aaagtgttgg gtgaaactaa   5520
aatcgaacta gcataatact gtacagtaat tcagttgttt ccttttaaat ataaataaaa   5580
tcaagcctga gtgccacaac tctatggagc actccatctg ttcttttata tttgtcgtca   5640
cgtcgaccaa actttctcat ttttaactaa gtttatataa aagattaaca atatttgtat   5700
ctctaaataa atttacataa aaatagattc agtgatctct aattatatat actaattacg   5760
tgtcacaaat attaatattt tttatatatt taatcaaagt taattacgtc aaatgaaatg   5820
atcagtgccc ggcagttcca taccacactt tcacggcacc acttcctccg aacaaaacgt   5880
atcctaaaaa aagaaaaaat cctttggatt ctgtctctct tagcttaaat atcctcgact   5940
tgacagtgtt tgcattttct tgtttttttct ctaagatttg atgatgttgt tattttagta   6000
gtataagcga catgcccttt gacaatgagg cgtccatggt agatttctat caatttcaaa   6060
atttgttgga ctctagctca atgttttcga aatgctcgta gaggtaaagt gtttatatgt   6120
atgttcacgt gagcctgcat ctttaacgtg atttgaaaga agaaaaaacc ttcgtcatgt   6180
ggctcatcat cagggttcaa gtactacctt gctttagttt tgattgttgt ggaggttaat   6240
gactaattta gaggtgttaa catgtctttc taaaaacttg caaagttaga atgttaatt   6300 tagtagcaag cacacacccc aaactcttcc ctctccatgt ggctagctgg gctggaggct   6360
gcctgcctgc ctatataagg atgggttgct cggccacttg tcacacccac tccatcacca   6420
gttcaccact cgtccgcttc accaacctat agagtttatg ccccgtcttg ctcttcagct   6480
ctggttagtc attaagagtc tgtttagatc tcaaattttt acatctcaaa acttttggct   6540
ctaaagttta catttcaaat aggtgttttg atgctttcca aattttttctg gtctgcaaca   6600 cacaagacac ggcccccctaa gcaagtttac acagtttgag ggctccaagg tccaaaattc   6660
caaatcttta caacctaagt gttacaggcc ctctttagat ccattcttct aaaaagtgcc   6720 cattttttcca aaagttttgg ctgtttagct gcatctggcg taattatcct gttattttat   6780
tcctctatga tgatgtagga gcatatatta ctgcacaagt ccttgttaat taatttgaga   6840
cagtcaggta ttagagggta gtagtagaac aacaagtggc caagtgggtg atcataagtc   6900
agttgttttt ttcttgaaaa tgctgttgtt atcactgatc gaatggttaa tgtgccgtat   6960
tgtagtgctt gcaaggtttg tagctaggcc gacatggagg aacaccggtc accagctcac   7020
gccaagcccg aggccgagca gccaccgcag cagcaggtgc cggcggcgat ggcggtggca   7080
gtggcagtgg acgtcgctgc tccagcagcg ctacagaata gtactgcggc tcctgctgag   7140 aacgggacg tcgctgctgc gggcgcggca gagaatggta ctgcggcttc cgctgcgaac   7200
ggggacggcg gcggctcgga gctgctcggc ggtccacgct ggacggggct gcaccttttc   7260
gtgatgaaca tccggagcgt gttcaagctg acgagctcg gcgcggaggt gctgggcatc   7320
gcggtgccgg cgtcgctggc gctgacggcc gacccgctcg cctcgctgat cgacacggcc   7380
ttcatcggcc ggctggggtc cgtggagatc gcggccgtgg gcgtcgccat cgcggtgttc   7440
aaccaggtca tgaaggtgtg catctacccg ctcgtcagcg tcaccacgtc gttcgtcgcg   7500
gaggaggacg ccgtgctcag caaaggcggc gccaaggtca tcgacaacgg agaagaagaa   7560
gaagaattag aagcgggaca agttggcccg gagaagcaca ctgccgctgc cggcgcggac   7620
```

```
ccggagaagc agcagcagcc agctgatgaa gaagccgcca agaacggcgg cgagggatgc    7680
gccccctgccg tcgtcgccgg ccggagtagc ggcaagaaat cagggaacag gaggttcgtg   7740
ccgtccgtga cgtcggcact gatcgtgggc gcgctcctgg ggctgttcca gaccgtcttc    7800
ctcgtcgccc ccgggaagcc gctgctgcgc ctcatgggcg tcaagccggt aagttactgt    7860
gcctgtgcgt gcccgcaccg catgcaacgg tgaactagat tcgtcggtgc aacgacgaac    7920
aattgcttat acaatttact ggtgatattc gaatgatttc ccagggttcg cccatggtga    7980
tgcccgcgct cgcgctacctg acgctgcgcg cgcttggcgc cccggccgtg ctgctgtctc    8040
tcgccatgca aggagtcttc cgtgggttca aggacgccaa gacgccctta tacgccatcg     8100
gtaaccaata atgctccata catgatacat acaatgcggc catatatgtc aaccaggcaa    8160
accagcatgg tttttcggt aaagtttatt ttgcccttga gggcatgtgt ccttactctc     8220
tcatccattg gattcgcttt gagaaatgtg caaacacaca tctcaaagcg aaactacttt    8280
gatatgtatg tttgcacact tctcaaaacg aatctaatgg gtgggagagc gagagtatct    8340
gcccttaagg gaaaaaaaac acccacgcac gtttgatctg agctgtgtta cgaatgaatg    8400
catgcagtgg ccggcgacgc ggcgaacatt gtgctggatc cgatcctgat atttggctgc    8460
cgcctgggcg tgatcggcgc agccattgcc catgttcttt cccagtataa gaccatgacc   8520
acccatctcc ttcttgtcag caattcagca ttggccgcaa caactgacaa tggcgaaatt    8580
aaaccgcacg tacgcaggta cctgataacg ctgataatgc tgagcaagct ggtgaggaag    8640
gtcgatgtcg tcccgcccag cctgaaatgc ctcaaattcc ggcgcttcct cggatgcggt    8700
cagtagtcga tcagtaggat ttggatccat taacaagacg agatgatgac gaggttataa    8760
tattgaccct gtatatgtgt gtataggatt ccttctgctg gcacgggtgg tggccgtgac    8820
gttctgcgtg acgctggcgg cgtcgctggc tgctcgccac gggccgaccg ccatggccgc    8880
cttccagatc tgcacccagg tctggctggc cacgtccctc ctcgccgacg ggctcgccgt    8940
cgccggccag gccatgatcg cgagcgcctt cgccaaggag gaccgctaca aggtggccgc    9000
caccgccgcg cgcgtcctgc agctcggcgt cgtcctgggc gccgccctca cggcgctcct    9060
cggactcggg ctgcagttcg gagccggcgt cttcaccagc gacgccgccg tcatcaagac    9120
catccggaag ggcgttccgt tcgtcgccgg cacgcagacg ctcaacacgc tagccttcgt    9180
cttcgacggc atcaacttcg gcgcgtcgga ctacgccttc tctgcctact ccatgatcgg    9240
cgtggcgggct gtcagcatcc cgtcgctcat cttcctctcg tcgcacggcg gcttcgtcgg    9300
catctgggta gcccctcacca tctacatggg cgtcagggcc cttgccagca cctggaggat    9360
ggcagcagcc caggggccat ggaagtttct tcggcagtga gcatatacgt acagtctcgt    9420
gtcgatcgta ctttaccttg attttagttt tatttcttat ttgtaaccga aggatactgg    9480
ctacttgcaa agcctaaatg ttctaatgta actagaaaca aatagtcatg atgaaaacaa    9540
tatggttagc atttctagca acgctattta cacgagtcat cttgtttgat ttttttaat    9600
aaataatttt aagaaagaag tgagtatatg agttacacaa taacacgcac aacccaaacg    9660
accctagtac gtagagattg gaatgaatcc aagaatagac ttacacacaa gaccagctgg    9720
tgccgtcaca tgcgtctgat cgaaaacaag attaatcaaa agaaagaaaa acaccgaag    9780
ccagcaatgc aacacaagca cagatcaaga aagaaacagg ggactttgac agccacgcgg    9840
cagcaactaa tacgccgatc gagctccggc cgacgttgtc ccacggtcgt cgtcgtcgtc    9900
gatcgcatgt agatatagta gtacggtaac gctgcgtggt gagaggcgag gcatgtggcc    9960
ggcaggcagg catgggttg                                                 9979
```

<210> SEQ ID NO 3
<211> LENGTH: 1803
<212> TYPE: DNA
<213> ORGANISM: Sorghum bicolor

<400> SEQUENCE: 3

| | | | | | |
|---|---|---|---|---|---|
| atggaggaac | accggtcacc | agctcacgcc | aagcccgagg | ccgagcagcc | accgcagcag | 60 |
| caggtgccgg | cggcgatggc | ggtggcagtg | gcagtggacg | tcgctgctcc | agcagcgcta | 120 |
| cagaatagta | ctgcggctcc | tgctgagaac | ggggacgtcg | ctgctgcggg | cgcggcagag | 180 |
| aatggtactg | cggcttccgc | tgcgaacggg | gacggcggcg | gctcggagct | gctcggcggt | 240 |
| ccacgctgga | cggggctgca | cctttttcgtg | atgaacatcc | ggagcgtgtt | caagctggac | 300 |
| gagctcggcg | cggaggtgct | gggcatcgcg | gtgccggcgt | cgctggcgct | gacggccgac | 360 |
| ccgctcgcct | cgctgatcga | cacggccttc | atcggccggc | tggggtccgt | ggagatcgcg | 420 |
| gccgtgggcg | tcgccatcgc | ggtgttcaac | caggtcatga | aggtgtgcat | ctacccgctc | 480 |
| gtcagcgtca | ccacgtcgtt | cgtcgcggag | gaggacgccg | tgctcagcaa | aggcggcgcc | 540 |
| aaggtcatcg | acaacggaga | agaagaagaa | gaattagaag | cgggacaagt | tggcccggag | 600 |
| aagcacactg | ccgctgccgg | cgcggacccg | gagaagcagc | agcagccagc | tgatgaagaa | 660 |
| gccgccaaga | acggcggcga | gggatgcgcc | cctgccgtcg | tcgccggccg | gagtagcggc | 720 |
| aagaaatcag | gaacaggag | gttcgtgccg | tccgtgacgt | cggcactgat | cgtgggcgcg | 780 |
| ctcctggggc | tgttccagac | cgtcttcctc | gtcgccgccg | ggaagccgct | gctgcgcctc | 840 |
| atgggcgtca | gccgggttc | gcccatggtg | atgcccgcgc | tgcgctacct | gacgctgcgc | 900 |
| gcgcttggcg | ccccggccgt | gctgctgtct | ctcgccatgc | aaggagtctt | ccgtgggttc | 960 |
| aaggacgcca | agacgccctt | atacgccatc | gtggccggcg | acgcggcgaa | cattgtgctg | 1020 |
| gatccgatcc | tgatatttgg | ctgccgcctg | gcgtgatcg | gcgcagccat | tgcccatgtt | 1080 |
| ctttcccagt | acctgataac | gctgataatg | ctgagcaagc | tggtgaggaa | ggtcgatgtc | 1140 |
| gtcccgccca | gctgaaatg | cctcaaattc | cggcgcttcc | tcggatgcgg | attccttctg | 1200 |
| ctggcacggg | tggtggccgt | gacgttctgc | gtgacgctgg | cggcgtcgct | ggctgctcgc | 1260 |
| cacgggccga | ccgccatggc | cgccttccag | atctgcaccc | aggtctggct | ggccacgtcc | 1320 |
| ctcctcgccg | acgggctcgc | cgtcgccggc | caggccatga | tcgcgagcgc | cttcgccaag | 1380 |
| gaggaccgct | acaaggtggc | cgccaccgcc | gcgcgcgtcc | tgcagctcgg | cgtcgtcctg | 1440 |
| ggcgccgccc | tcacggcgct | cctcggactc | gggctgcagt | tcggagccgg | cgtcttcacc | 1500 |
| agcgacgccg | ccgtcatcaa | gaccatccgg | aagggcgttc | cgttcgtcgc | cggcacgcag | 1560 |
| acgctcaaca | cgctagcctt | cgtcttcgac | ggcatcaact | tcggcgcgtc | ggactacgcc | 1620 |
| ttctctgcct | actccatgat | cggcgtggcg | gctgtcagca | tcccgtcgct | catcttcctc | 1680 |
| tcgtcgcacg | gcggcttcgt | cggcatctgg | gtagccctca | ccatctacat | gggcgtcagg | 1740 |
| gcccttgcca | gcacctggag | gatggcagca | gcccaggggc | catggaagtt | tcttcggcag | 1800 |
| tga | | | | | | 1803 |

<210> SEQ ID NO 4
<211> LENGTH: 322
<212> TYPE: PRT
<213> ORGANISM: Sorghum bicolor

<400> SEQUENCE: 4

```
Met Glu Glu His Arg Ser Pro Ala His Ala Lys Pro Glu Ala Glu Gln
1               5                   10                  15

Pro Pro Gln Gln Gln Val Pro Ala Ala Met Ala Val Ala Val Ala Val
            20                  25                  30

Asp Val Ala Ala Pro Ala Ala Leu Gln Asn Ser Thr Ala Ala Pro Ala
        35                  40                  45

Glu Asn Gly Asp Val Ala Ala Gly Ala Ala Glu Asn Gly Thr Ala
    50                  55                  60

Ala Ser Ala Ala Asn Gly Asp Gly Gly Ser Glu Leu Leu Gly Gly
65                  70                  75                  80

Pro Arg Trp Thr Gly Leu His Leu Phe Val Met Asn Ile Arg Ser Val
                85                  90                  95

Phe Lys Leu Asp Glu Leu Gly Ala Glu Val Leu Gly Ile Ala Val Pro
            100                 105                 110

Ala Ser Leu Ala Leu Thr Ala Asp Pro Leu Ala Ser Leu Ile Asp Thr
        115                 120                 125

Ala Phe Ile Gly Arg Leu Gly Ser Val Glu Ile Ala Ala Val Gly Val
130                 135                 140

Ala Ile Ala Val Phe Asn Gln Val Met Lys Val Cys Ile Tyr Pro Leu
145                 150                 155                 160

Val Ser Val Thr Thr Ser Phe Val Ala Glu Glu Asp Ala Val Leu Ser
                165                 170                 175

Lys Gly Gly Ala Lys Val Ile Asp Asn Gly Glu Glu Glu Glu Leu
            180                 185                 190

Glu Ala Gly Gln Val Gly Pro Glu Lys His Thr Ala Ala Ala Gly Ala
        195                 200                 205

Asp Pro Glu Lys Gln Gln Pro Ala Asp Glu Ala Ala Lys Asn
210                 215                 220

Gly Gly Glu Gly Cys Ala Pro Ala Val Val Ala Gly Arg Ser Ser Gly
225                 230                 235                 240

Lys Lys Ser Gly Asn Arg Arg Phe Val Pro Ser Val Thr Ser Ala Leu
                245                 250                 255

Ile Val Gly Ala Leu Leu Gly Leu Phe Gln Thr Val Phe Leu Val Ala
            260                 265                 270

Ala Gly Lys Pro Leu Leu Arg Leu Met Gly Val Lys Pro Gly Ser Pro
        275                 280                 285

Met Val Met Pro Ala Leu Arg Tyr Leu Thr Leu Arg Ala Leu Gly Ala
        290                 295                 300

Pro Ala Val Leu Leu Ser Leu Ala Met Gln Gly Val Phe Arg Gly Phe
305                 310                 315                 320

Lys Asp

<210> SEQ ID NO 5
<211> LENGTH: 455
<212> TYPE: DNA
<213> ORGANISM: Sorghum bicolor

<400> SEQUENCE: 5
ggatccagtg agctaccggt gaaggtgctc gttatgcgtt taaacattgt tccgtccggc      60
ggcatctagc taggagtact cctacagact attaaagttg gccttgtttt agttccaaat    120
aattttgcaa aataggaata gtagcatttt cgtttgtatt tgacaaatat tgtccaatca    180
tgaactaatt agactcaaaa gattcgtctc gttaatttcg accaaactgt gaaattagtt    240 tttatttttcg tctatatttta atacttcatg catgcgtcta aagatttgat gtgacggaga    300
```

-continued

```
atctaaaaaa ttttgcaaaa cttttttggga actaaacaag gccttggttg gtgcgatgat    360
gttggatcca gtgagctacc ggtgaaggtg ctcgttatgc gtttaaacat tgttccgtcc    420
ggcggcatct atactcctac agactattaa agttg                                455
```

<210> SEQ ID NO 6
<211> LENGTH: 1181
<212> TYPE: DNA
<213> ORGANISM: Sorghum bicolor

<400> SEQUENCE: 6

```
ggatccagtg agctaccggt gaaggtgctc gttatgcgtt taaacattgt tccgtccggc     60
ggcatctagc taggagtact cctacagact attaaagttg gccttgtttt agttccaaat    120
aattttgcaa ataggaata gtagcatttt cgtttgtatt tgacaaatat tgtccaatca    180
tgaactaatt agactcaaaa gattcgtctc gttaatttcg accaaactgt gaaattagtt    240
tttattttcg tctatattta atacttcatg catgcgtcta aagatttgat gtgacggaga    300
atctaaaaaa ttttgcaaaa cttttttggga actaaacaag gccttggttg gtgcgatgat    360
gttggatcca gtgagctacc ggtgaaggtg ctcgttatgc gtttaaacat tgttccgtcc    420
ggcggcatct agctaggagt actcctacag actattaaag ttgggccttg tttagttcca    480 ataattttg caaatagga aagtagcat ttcgtttgt atttgacaaa tattgtccaa    540
tcatgaacta attagactca aaagattcgt ctcgttaatt tcgaccaaac tgtgaaatta    600 gttttatt cgtctatat ttaatacttc atgcatgcgt ctaaagattt gatgtgacgg    660
agaatctaaa aaattttgca aactttttg ggaactaaac aaggccttgg ttggtgcgat    720
gatgttggat ccagtgagct accggtgaag gtgctcgtta tgcgtttaaa cattgttccg    780
tccggcggca tctagctagg agtactccta cagactatta agttgggcc ttgtttagtt    840 ccaaataatt ttgcaaaata ggaatagtag cattttcgtt tgtatttgac aaatattgtc    900
caatcatgaa ctaattagac tcaaaagatt cgtctcgtta atttcgacca aactgtgaaa    960 ttagtttta ttttcgtcta tatttaatac ttcatgcatg cgtctaaaga tttgatgtga    1020
cggagaatct aaaaaatttt gcaaaacttt ttgggaacta aacaaggcct tggttggtgc    1080
gatgatgttg gatccagtga gctaccggtg aaggtgctcg ttatgcgttt aaacattgtt    1140
ccgtccggcg gcatctatac tcctacagac tattaaagtt g                        1181
```

<210> SEQ ID NO 7
<211> LENGTH: 1540
<212> TYPE: DNA
<213> ORGANISM: Sorghum bicolor

<400> SEQUENCE: 7

```
ggatccagtg agctaccggt gaaggtgctc gttatgcgtt taaacattgt tccgtccggc     60
ggcatctagc taggagtact cctacagact attaaagttg gccttgtttt agttccaaat    120
aattttgcaa ataggaata gtagcatttt cgtttgtatt tgacaaatat tgtccaatca    180
tgaactaatt agactcaaaa gattcgtctc gttaatttcg accaaactgt gaaattagtt    240
tttattttcg tctatattta atacttcatg catgcgtcta aagatttgat gtgacggaga    300
atctaaaaaa ttttgcaaaa cttttttggga actaaacaag gccttggttg gtgcgatgat    360
gttggatcca gtgagctacc ggtgaaggtg ctcgttatgc gtttaaacat tgttccgtcc    420
ggcggcatct agctaggagt actcctacag actattaaag ttgggccttg tttagttcca    480
```

```
aataattttg caaaatagga atagtagcat tttcgtttgt atttgacaaa tattgtccaa    540
tcatgaacta attagactca aaagattcgt ctcgttaatt tcgaccaaac tgtgaaatta    600 gttttattt tcgtctatat ttaatacttc atgcatgcgt ctaaagattt gatgtgacgg     660
agaatctaaa aaattttgca aacttttg ggaactaaac aaggccttgg ttggtgcgat      720
gatgttggat ccagtgagct accggtgaag gtgctcgtta tgcgtttaaa cattgttccg    780
tccggcggca tctagctagg agtactccta cagactatta agttgggcc ttgtttagtt     840 ccaaataatt ttgcaaaata ggaatagtag cattttcgtt tgtatttgac aaatattgtc    900
caatcatgaa ctaattagac tcaaaagatt cgtctcgtta atttcgacca aactgtgaaa    960
ttagttttta ttttcgtcta tatttaatac ttcatgcatg cgtctaaaga tttgatgtga   1020
cggagaatct aaaaaatttt gcaaaacttt ttgggaacta aacaaggcct tggttggtgc   1080
gatgatgttg gatccagtga gctaccggtg aaggtgctcg ttatgcgttt aaacattgtt   1140
ccgtccggcg gcatctagct aggagtactc ctacagacta ttaaagttgg gccttgttta   1200
gttccaaata attttgcaaa ataggaatag tagcattttc gtttgtattt gacaaatatt   1260
gtccaatcat gaactaatta gactcaaaag attcgtctcg ttaatttcga ccaaactgtg   1320
aaattagttt ttattttcgt ctatatttaa tacttcatgc atgcgtctaa agatttgatg   1380
tgacggagaa tctaaaaaat tttgcaaaac ttttgggaa ctaaacaagg ccttggttgg    1440
tgcgatgatg ttggatccag tgagctaccg gtgaaggtgt tatgcgttta acattgttc     1500 cgtccggcgg catctatact cctacagact attaaagttg                         1540

<210> SEQ ID NO 8
<211> LENGTH: 1907
<212> TYPE: DNA
<213> ORGANISM: Sorghum bicolor

<400> SEQUENCE: 8
ggatccagtg agctaccggt gaaggtgctc gttatgcgtt taaacattgt tccgtccggc     60
ggcatctagc taggagtact cctacagact attaaagttg gccttgttt agttccaaat    120 aattttgcaa aataggaata gtagcatttt cgtttgtatt tgacaaatat tgtccaatca   180
tgaactaatt agactcaaaa gattcgtctc gttaatttcg accaaactgt gaaattagtt   240
tttattttcg tctatattta atacttcatg catgcgtcta aagatttgat gtgacggaga   300
atctaaaaaa ttttgcaaaa cttttggga actaaacaag gccttggttg gtgcgatgat    360
gttggatcca gtgagctacc ggtgaaggtg ctcgttatgc gtttaaacat tgttccgtcc   420
ggcggcatct agctaggagt actcctacag actattaaag ttgggccttg tttagttcca   480
aataattttg caaaatagga atagtagcat tttcgtttgt atttgacaaa tattgtccaa   540
tcatgaacta attagactca aaagattcgt ctcgttaatt tcgaccaaac tgtgaaatta   600 gttttattt tcgtctatat ttaatacttc atgcatgcgt ctaaagattt gatgtgacgg     660
agaatctaaa aaattttgca aacttttg ggaactaaac aaggccttgg ttggtgcgat      720
gatgttggat ccagtgagct accggtgaag gtgctcgtta tgcgtttaaa cattgttccg    780
tccggcggca tctagctagg agtactccta cagactatta agttgggcc ttgtttagtt     840 ccaaataatt ttgcaaaata ggaatagtag cattttcgtt tgtatttgac aaatattgtc    900
caatcatgaa ctaattagac tcaaaagatt cgtctcgtta atttcgacca aactgtgaaa    960
ttagttttta ttttcgtcta tatttaatac ttcatgcatg cgtctaaaga tttgatgtga   1020
cggagaatct aaaaaatttt gcaaaacttt ttgggaacta aacaaggcct tggttggtgc   1080
```

```
gatgatgttg gatccagtga gctaccggtg aagtgctcg ttatgcgttt aaacattgtt    1140
ccgtccggcg gcatctagct aggagtactc ctacagacta ttaaagttgg gccttgttta    1200
gttccaaata attttgcaaa ataggaatag tagcattttc gtttgtattt gacaaatatt    1260
gtccaatcat gaactaatta gactcaaaag attcgtctcg ttaatttcga ccaaactgtg    1320
aaattagttt ttattttcgt ctatatttaa tacttcatgc atgcgtctaa agatttgatg    1380
tgacggagaa tctaaaaaat tttgcaaaac ttttttgggaa ctaaacaagg ccttggttgg    1440
tgcgatgatg ttggatccag tgagctaccg gtgaaggtgc tcgttatgcg tttaaacatt    1500
gttccgtccg gcggcatcta gctaggagta ctcctacaga ctattaaagt tgggccttgt    1560
ttagttccaa ataattttgc aaataggaa tagtagcatt ttcgtttgta tttgacaaat    1620
attgtccaat catgaactaa ttagactcaa agattcgtc tcgttaattt cgaccaaact    1680
gtgaaattag tttttatttt cgtctatatt taatacttca tgcatgcgtc taaagatttg    1740
atgtgacgga gaatctaaaa aattttgcaa aacttttttgg gaactaaaca aggccttggt    1800
tggtgcgatg atgttggatc cagtgagcta ccggtgaagg tgctcgttat gcgtttaaac    1860
attgttccgt ccggcggcat ctatactcct acagactatt aaagttg                 1907
```

```
<210> SEQ ID NO 9
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 9
stgcagtatc tgcagtatca ttt                                             23

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 10
aatccgtcag gtcagcaatc                                                 20

<210> SEQ ID NO 11
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 11
aaggcaacaa ctgaggcact                                                 20

<210> SEQ ID NO 12
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 12
tcgctagagt ggtgcaagaa                                                 20

<210> SEQ ID NO 13
```

```
<211> LENGTH: 36
<212> TYPE: DNA
<213> ORGANISM: Artifical Sequence
<220> FEATURE:
<223> OTHER INFORMATION: Chemically Synthesized

<400> SEQUENCE: 13
gctgtcaacg atacgctacg taacggcatg acagtg                           36

<210> SEQ ID NO 14
<211> LENGTH: 23
<212> TYPE: DNA
<213> ORGANISM: Artifical Sequence
<220> FEATURE:
<223> OTHER INFORMATION: Chemically Synthesized

<400> SEQUENCE: 14
cgactggagc acgaggacac tga                                         23

<210> SEQ ID NO 15
<211> LENGTH: 21
<212> TYPE: DNA
<213> ORGANISM: Artifical Sequence
<220> FEATURE:
<223> OTHER INFORMATION: Chemically Synthesized

<400> SEQUENCE: 15
ataccgagga agcgccggaa t                                           21

<210> SEQ ID NO 16
<211> LENGTH: 27
<212> TYPE: DNA
<213> ORGANISM: Artifical Sequence
<220> FEATURE:
<223> OTHER INFORMATION: Chemically Synthesized

<400> SEQUENCE: 16
ggacactgac atggactgaa ggaggta                                     27

<210> SEQ ID NO 17
<211> LENGTH: 20
<212> TYPE: DNA
<213> ORGANISM: Artifical Sequence
<220> FEATURE:
<223> OTHER INFORMATION: Chemically Synthesized

<400> SEQUENCE: 17
ccttgaaccc acggaagact                                             20

<210> SEQ ID NO 18
<211> LENGTH: 25
<212> TYPE: DNA
<213> ORGANISM: Artifical Sequence
<220> FEATURE:
<223> OTHER INFORMATION: Chemically Synthesized

<400> SEQUENCE: 18
gctgtcaacg atacgctacg taacg                                       25

<210> SEQ ID NO 19
<211> LENGTH: 20
<212> TYPE: DNA
<213> ORGANISM: Artifical Sequence
<220> FEATURE:
<223> OTHER INFORMATION: Chemically Synthesized

<400> SEQUENCE: 19
```
gcccgcgctg cgctacctga                                                  20

<210> SEQ ID NO 20
<211> LENGTH: 23
<212> TYPE: DNA
<213> ORGANISM: Artifical Sequence
<220> FEATURE:
<223> OTHER INFORMATION: Chemically Synthesized

<400> SEQUENCE: 20
cgctacgtaa cggcatgaca gtg                                              23

<210> SEQ ID NO 21
<211> LENGTH: 24
<212> TYPE: DNA
<213> ORGANISM: Artifical Sequence
<220> FEATURE:
<223> OTHER INFORMATION: Chemically Synthesized

<400> SEQUENCE: 21
acgctgataa tgctgagcaa gctg                                             24

<210> SEQ ID NO 22
<211> LENGTH: 27
<212> TYPE: DNA
<213> ORGANISM: Artifical Sequence
<220> FEATURE:
<223> OTHER INFORMATION: Chemically Synthesized

<400> SEQUENCE: 22
gtacgatcga cacgagaact gtacgta                                          27

<210> SEQ ID NO 23
<211> LENGTH: 27
<212> TYPE: DNA
<213> ORGANISM: Artifical Sequence
<220> FEATURE:
<223> OTHER INFORMATION: Chemically Synthesized

<400> SEQUENCE: 23
tgcttgcaag gtttgtagct aggccga                                          27

<210> SEQ ID NO 24
<211> LENGTH: 296
<212> TYPE: PRT
<213> ORGANISM: Arabidopsis sp.

<400> SEQUENCE: 24

Arg Asn Ile Pro Ser Ala Ser Ser Ala Leu Ile Ile Gly Gly Val Leu
1               5                   10                  15

Gly Leu Phe Gln Ala Val Phe Leu Ile Ser Ala Ala Lys Pro Leu Leu
            20                  25                  30

Ser Phe Met Gly Val Lys His Asp Ser Pro Met Met Arg Pro Ser Gln
        35                  40                  45

Arg Tyr Leu Ser Leu Arg Ser Leu Gly Ala Pro Ala Val Leu Leu Ser
    50                  55                  60

Leu Ala Ala Gln Gly Val Phe Arg Gly Phe Lys Asp Thr Thr Thr Pro
65                  70                  75                  80

Leu Phe Ala Thr Val Ile Gly Asp Val Thr Asn Ile Ile Leu Asp Pro
                85                  90                  95

Ile Phe Ile Phe Val Phe Arg Leu Gly Val Thr Gly Ala Ala Thr Ala
                100                 105                 110

```
His Val Ile Ser Gln Tyr Leu Met Cys Gly Ile Leu Leu Trp Lys Leu
            115                 120                 125

Met Gly Gln Val Asp Ile Phe Asn Met Ser Thr Lys His Leu Gln Phe
        130                 135                 140

Cys Arg Phe Met Lys Asn Gly Phe Leu Leu Met Arg Val Ile Ala
145                 150                 155                 160

Val Thr Phe Cys Val Thr Leu Ser Ala Ser Leu Ala Ala Arg Glu Gly
                165                 170                 175

Ser Thr Ser Met Ala Ala Phe Gln Val Cys Leu Gln Val Trp Leu Ala
            180                 185                 190

Thr Ser Leu Leu Ala Asp Gly Tyr Ala Val Ala Gly Gln Ala Ile Leu
        195                 200                 205

Ala Ser Ala Phe Ala Lys Lys Asp Tyr Lys Arg Ala Ala Ala Thr Ala
    210                 215                 220

Ser Arg Val Leu Gln Leu Gly Leu Val Leu Gly Phe Val Leu Ala Val
225                 230                 235                 240

Ile Leu Gly Ala Gly Leu His Phe Gly Ala Arg Val Phe Thr Lys Asp
                245                 250                 255

Asp Lys Val Leu His Leu Ile Ser Ile Gly Leu Pro Phe Val Ala Gly
            260                 265                 270

Thr Gln Pro Ile Asn Ala Leu Ala Phe Val Phe Asp Gly Val Asn Phe
        275                 280                 285

Gly Ala Ser Asp Phe Gly Tyr Ala
    290                 295

<210> SEQ ID NO 25
<211> LENGTH: 296
<212> TYPE: PRT
<213> ORGANISM: Oryza sp.

<400> SEQUENCE: 25

Arg Phe Val Pro Ser Val Thr Ser Ala Leu Ile Val Gly Ala Phe Ile
1               5                   10                  15

Gly Leu Leu Gln Ala Val Phe Leu Val Ala Ala Gly Lys Pro Leu Leu
            20                  25                  30

Arg Ile Met Gly Val Lys Pro Gly Ser Pro Met Met Ile Pro Ala Leu
        35                  40                  45

Arg Tyr Leu Val Val Arg Ser Leu Gly Ala Pro Ala Val Leu Leu Ser
    50                  55                  60

Leu Ala Met Gln Gly Val Phe Arg Gly Phe Lys Asp Thr Lys Thr Pro
65                  70                  75                  80

Leu Tyr Ala Thr Val Thr Gly Asp Leu Ala Asn Ile Ala Leu Asp Pro
                85                  90                  95

Ile Leu Ile Phe Thr Cys Arg Phe Gly Val Gly Ala Ala Ile Ala
            100                 105                 110

His Val Ile Ser Gln Tyr Leu Ile Thr Leu Ile Met Leu Cys Lys Leu
            115                 120                 125

Val Arg Lys Val Asp Val Ile Pro Ser Ser Leu Lys Ser Leu Lys Phe
        130                 135                 140

Arg Arg Phe Leu Gly Cys Gly Phe Leu Leu Leu Ala Arg Val Val Ala
145                 150                 155                 160

Val Thr Phe Cys Val Thr Leu Ala Ala Ser Leu Ala Ala Arg His Gly
                165                 170                 175

Ala Thr Ala Met Ala Ala Phe Gln Ile Cys Ala Gln Val Trp Leu Ala
```

-continued

```
            180                 185                 190
Ser Ser Leu Leu Ala Asp Gly Leu Ala Val Ala Gly Gln Ala Leu Leu
        195                 200                 205

Ala Ser Ala Phe Ala Lys Lys Asp His Tyr Lys Val Ala Val Thr Thr
    210                 215                 220

Ala Arg Val Leu Gln Leu Ala Val Val Leu Gly Val Gly Leu Thr Ala
225                 230                 235                 240

Phe Leu Ala Ala Gly Met Trp Phe Gly Ala Gly Val Phe Thr Ser Asp
                245                 250                 255

Ala Ala Val Ile Ser Thr Ile His Arg Gly Val Pro Phe Val Ala Gly
            260                 265                 270

Thr Gln Thr Ile Asn Thr Leu Ala Phe Val Phe Asp Gly Val Asn Phe
        275                 280                 285

Gly Ala Ser Asp Tyr Ala Phe Ala
    290                 295
```

<210> SEQ ID NO 26
<211> LENGTH: 20
<212> TYPE: DNA
<213> ORGANISM: Artifical Sequence
<220> FEATURE:
<223> OTHER INFORMATION: Chemically Synthesized

<400> SEQUENCE: 26
gtgctggatc cgatcctgat                                              20

<210> SEQ ID NO 27
<211> LENGTH: 20
<212> TYPE: DNA
<213> ORGANISM: Artifical Sequence
<220> FEATURE:
<223> OTHER INFORMATION: Chemically Synthesized

<400> SEQUENCE: 27
cactgccgaa gaaacttcca                                              20

<210> SEQ ID NO 28
<211> LENGTH: 20
<212> TYPE: DNA
<213> ORGANISM: Artifical Sequence
<220> FEATURE:
<223> OTHER INFORMATION: Chemically Synthesized

<400> SEQUENCE: 28
tgatgaagat tctcactgag                                              20

<210> SEQ ID NO 29
<211> LENGTH: 21
<212> TYPE: DNA
<213> ORGANISM: Artifical Sequence
<220> FEATURE:
<223> OTHER INFORMATION: Chemically Synthesized

<400> SEQUENCE: 29
gatccacaat ctgttggaac g                                            21

<210> SEQ ID NO 30
<211> LENGTH: 21
<212> TYPE: DNA
<213> ORGANISM: Artifical Sequence
<220> FEATURE:
<223> OTHER INFORMATION: Chemically Synthesized -continued

```
<400> SEQUENCE: 30
cagccattgc ccatgttctt t                                                    21

<210> SEQ ID NO 31
<211> LENGTH: 22
<212> TYPE: DNA
<213> ORGANISM: Artifical Sequence
<220> FEATURE:
<223> OTHER INFORMATION: Chemically Synthesized

<400> SEQUENCE: 31
accagcttgc tcagcattat ca                                                   22

<210> SEQ ID NO 32
<211> LENGTH: 18
<212> TYPE: DNA
<213> ORGANISM: Artifical Sequence
<220> FEATURE:
<223> OTHER INFORMATION: Chemically Synthesized

<400> SEQUENCE: 32
cccagtacct gataacgc                                                        18

<210> SEQ ID NO 33
<211> LENGTH: 32
<212> TYPE: DNA
<213> ORGANISM: Artifical Sequence
<220> FEATURE:
<223> OTHER INFORMATION: Chemically Synthesized

<400> SEQUENCE: 33
aatatctaga cgatcgacac gagactgtac gt                                        32

<210> SEQ ID NO 34
<211> LENGTH: 30
<212> TYPE: DNA
<213> ORGANISM: Artifical Sequence
<220> FEATURE:
<223> OTHER INFORMATION: Chemically Synthesized

<400> SEQUENCE: 34
aatacccggg aaggtttgta gctaggccga                                           30
```

SORGHUM ALUMINUM TOLERANCE GENE, SBMATE

BACKGROUND OF THE INVENTION

1. Field of the Invention

This invention relates to a major aluminum tolerance gene, SbMATE (for *Sorghum bicolor* member of the multidrug and toxic compound extrusion transporter family), that is responsible for the $Alt_{SB}$ locus (for aluminum tolerance in *Sorghum bicolor*), cloned from sorghum along with its native promoter and regulatory regions, a construct containing the gene and a constitutive promoter, a vector containing the construct, and a method of transforming a plant utilizing the construct and vector, and plants, including staple crop plants, transformed with the gene construct having increased tolerance to aluminum toxicity.

2. Description of the Relevant Art

The tropics and subtropics are extremely important food producing regions, particularly for many developing countries. However, agriculture on the acid soils that are prevalent in these areas is seriously challenged by limitations to plant yield caused by drought, mineral nutrient deficiencies such as phosphorus deficiency, and in particular, aluminum toxicity. Aluminum (Al) is ubiquitous in soils and, at pH values below 5.0, is solubilized into the soil solution as the highly phytotoxic $Al^{3+}$ species, which inhibits root growth and damages root systems (Kochian, L. V. 1995. *Annu. Rev. Plant Biol.* 46: 237-260). Hence, aluminum toxicity is a primary limitation for crop production in many developing countries, including 38% of the farmland in Southeast Asia, 31% in Latin America and 20% of the arable lands in East Asia and Sub-Saharan Africa (Wood et al. 2000. In *Pilot Analysis of Global Ecosystems: Agroecosystems*, International Food Policy Research Institute and the World Resources Institute, Washington, D.C.), thus reducing food security in parts of the world where it is most tenuous.

A major aluminum tolerance mechanism has been identified in plants based on aluminum-activated organic acid release from the root apex, which is the site of aluminum phytotoxicity (Ryan et al. 1993. *J. Exp. Bot.* 44: 437-446). Depending on the plant species, the organic acids malate, citrate, or oxalate are released from the roots in response to aluminum exposure and form stable, nontoxic complexes with $Al^{3+}$ cations (Ma et al. 2001. *Trends Plant Sci.* 6: 273-278). A considerable body of physiological evidence in support of this mechanism exists in the literature (see Kochian et al. 2004. *Annu. Rev. Plant Biol.* 55: 459-493 and references therein) and it is now generally accepted that with regards to this Al tolerance mechanism, aluminum activates a plasma membrane organic acid transporter, and that this transporter plays a central role in aluminum tolerance (Delhaize and Ryan. 1995. *Plant Physiol.* 107: 315-321; Ryan et al. 2001. *Annu. Rev. Plant Physiol. Plant Mol. Biol.* 52: 527-560; Kochian et al. 2004, supra).

Recently, the first aluminum (Al) tolerance gene, ALMT1, was isolated and shown to encode an Al activated malate transporter (Sasaki et al. 2004. *Plant J.* 37: 645-653). ALMT1 was found to be a member of a novel family of membrane proteins, and based on genetic mapping of the ALMT1 gene, it was shown to most likely correspond to $Alt_{BH}$, a major Al tolerance locus in wheat and other members of the Tritceae tribe (Sasaki et al., supra; Raman et al. 2005. *Genome* 48: 781-791). Subsequently, a homolog of ALMT1 was shown to also confer Al tolerance via Al-activated root malate exudation in *Arabidopsis* (Hoekenga et al. 2006. *Proc. Natl. Acad. Sci. USA* 103: 9738-9743).

A second constraint on acid soils is phosphorous (P) deficiency, which is caused by P fixation with Al and Fe oxides on the surface of clay minerals in acid soils. Hence P availability is a second major factor limiting crop production on acid soils (Sanchez et al. 1997. In: *Replenishing Soil Fertility in Africa*, ed. R Buresh, P Sanchez, F Calhoun, pp. 1-46). Because of the low availability of this essential mineral nutrient, P, plants have evolved a number of adaptive mechanisms to acquire P from the soil. One major such adaptive mechanism is the release of organic acids, primarily citrate and malate, from roots (Neumann G. and Martinoia, E. 2002. *Trends Plant Sci.* 7: 162-167). These released organic acids can desorb P from mineral surfaces, solubilizing it from associations with Al, Fe and Ca oxides and hydroxides via metal complexation. Hence, a transporter such as SbMATE that can facilitate the efflux of citric acid from roots could significantly increase the ability of crop plants to acquire P from acid soils with low P availability.

There is a real need in both developing and developed countries to better understand Al tolerance mechanisms and associated genes and their effect on crop plants. Genes that confer enhanced, Al-activated organic acid (citrate, malate, or oxalate) release to crop plants need to be identified and evaluated for their effect in enabling increased Al tolerance in a wide range of crop species grown in acid soils worldwide. The utilization of genes which contribute to a plant's tolerance to the Al present in acid soils results in transgenic plants with a mechanism for achieving high yield in acid soils where soluble $Al^{3+}$ are found. Thus, such genes and constructs can ensure yield stability for plants grown on acid soils, i.e., Al-tolerant plants make possible the utilization of marginal lands for agriculturally and commercially important staple crop production.

SUMMARY OF THE INVENTION

We have expressed the isolated SbMATE gene from sorghum in *Arabidopsis* and confirmed that its expression results in the induction of aluminum tolerance in the transformed plants.

In accordance with this discovery, it is an object of the invention to provide an isolated nucleic acid construct containing a DNA sequence which encodes the SbMATE protein involved in the regulation of aluminum tolerance in plants.

It is a further object of the invention to provide a recombinant nucleic acid molecule construct comprising a nucleic acid molecule upstream of the recombinant SbMATE cDNA. This upstream nucleic acid sequence ends at a 7 bp insertion/deletion polymorphism (7 bp indel in FIG. 1) genetically flanking $Alt_{SB}$. This region harbors a polymorphic miniature inverted repeated element (MITE) insertion and a tissue-specific, Al-inducible promoter, operatively linked so that the promoter enhances transcription of the SbMATE coding sequence in a host cell. Additional sequences downstream of SbMATE up to a SNP G/A (SNP G/A in FIG. 1) genetically flanking $Alt_{SB}$ at the 3' end of the gene may also be involved in expression of the $Alt_{SB}$ coding region.

It is a still further object of the invention to provide a vector which comprises a construct which is capable of expressing the SbMATE gene.

It is another object of the invention to provide a host cell comprising the vector capable of expressing the SbMATE gene or progeny of said host cell.

It is an additional object of the invention to provide a transgenic plant cell and plant containing the nucleic acid construct and having an improved tolerance to aluminum.

It is another object of the invention to provide a method of manipulating aluminum tolerance in plants by stably transforming a plant with an isolated nucleotide molecule capable of modulating aluminum tolerance, operably linked with a promoter capable of driving expression of a gene in a plant cell.

It is a further object of the invention to provide a method of facilitating the efflux of citric acid from roots of plants, thus increasing the ability of crop plants to acquire phosphorous from acid soils by stably transforming a plant with an isolated nucleotide molecule capable of modulating citrate exudation, operably linked with a promoter capable of driving expression of a gene in a plant cell.

It is a still further object of the invention to provide a root-specific, Al-inducible promoter to drive the expression of SbMATE in a plant cell.

It is yet another object of the invention to provide a method of increasing Al tolerance of a plant comprising transforming the SbMATE gene into a plant by introducing a vector, wherein said vector comprises an effective amount of a nucleic acid construct, which is a DNA sequence which is capable of transforming the SbMATE gene into a plant.

It is yet another object of the invention to provide plants, plant cells, and plant parts, which have been transformed by the SbMATE gene-containing construct of the invention, with enhanced aluminum tolerance when compared to plants of the same species which have not been transformed.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1a shows the genetic and physical map of the $Alt_{SB}$ region on chromosome 3. The marker T755 corresponds to the leftmost end of BAC 55D12. Dotted lines indicate the approximate physical position of genetic markers in the sorghum BAC contig. FIG. 1b depicts the high resolution map of $Alt_{SB}$ on BAC 181g10 (bold line). Broad horizontal arrows indicate ORF (1 to 16) positions and their predicted transcriptional orientations. Numbers between downward arrows below 181g10 indicate the distribution of the 27 single recombination events detected by high-resolution mapping. The target 24.6 Kb region that contains ORFs 7, 8 and 9 (candidates for $Alt_{SB}$) is marked along with the flanking markers (7 bp indel and a G/A SNP). FIG. 1c depicts the semi-quantitative RT-PCR of ORFs 8 and 9 in roots and shoots of the Al tolerant (T) and sensitive (S) NIL's in response to the presence (+) or absence (−) of {27} μM $Al^{3+}$. FIG. 1d shows the target 24.6 Kb region from the Al tolerant (SC283) and sensitive (BR007) parents with polymorphisms shown inside dotted diamonds. The genomic $Alt_{SB}$ (ORF7) is 2407 bp long and contains 5 exons (gray boxes) and 4 introns (black bold lines).

FIG. 3a shows the spatial analysis of SbMATE expression in different root regions of Al-tolerant (T) and Al-sensitive (S) NIL's grown on hydroponic nutrient solution with (+, solid bars) or without (−, open bars) {27} μM $Al^{3+}$ for 3 days. SbMATE relative expression values were determined using quantitative real-time PCR and are the means ±s.d. of 3 replicate experiments. FIG. 3b shows the daily root growth rate (left panel) and Al-activated root citrate exudation (right panel) for Al tolerant (T) and sensitive (S) NIL's+/−{27} μM $Al^{3+}$ for 1, 3 and 6 days. FIG. 3c depicts SbMATE expression within the root apex of the tolerant (T) and sensitive (S) NIL's exposed to +/−{27} μM $Al^{3+}$ for 1, 3, and 6 days using quantitative real-time PCR. The data are the means ±s.d. for 3 replicate experiments in FIGS. 3a and 3c, and 4 replicates for the organic acid determinations and 8 replicate root growth measurements in FIG. 3b. FIG. 3d depicts membrane localization of the SbMATE protein in epidermal onion cells. The upper panels show the GFP fluorescence patterns for SbMATE::GFP (i, ii) and cytoplasmic GFP (iii, iv). The lower set of figures (v-viii) show the overlay of bright field and GFP fluorescence images for the same specimens. The images were acquired prior (first and third columns) and following (second and fourth columns) cell plasmolysis (onion epidermal strips exposed to 1 M sucrose). The fluorescence associated with SbMATE is localized to the plasma membrane (i, v); following cell plasmolysis the SbMATE fluorescence signal is associated with the retracted plasma membrane (ii, vi). Scale bar=50 μm and images are representative of three independent replicate experiments. PM: plasma membrane, CW: cell wall.

FIG. 4a shows SbMATE expression relative to that of the Actin gene (assessed by semi-quantitative RT-PCR) vs. Al tolerance (Relative Net Root Growth, RNRG); FIG. 4b shows SbMATE relative expression vs. root citrate exudation; FIG. 4c depicts root citrate exudation vs. Al tolerance and FIG. 4d, Al tolerance vs. the size of the region within the putative SbMATE promoter harboring the MITE insertion (bp, base pairs). Correlation coefficients (r) and probability (P) values are shown. FIG. 4e shows the structure and size of the MITE insertion region in 4 sorghum lines that are representatives for each of the 4 size classes shown in FIG. 4d.

FIG. 6a depicts Al tolerance (root growth in nutrient solution+1.5 μM $Al^{3+}$ activity) for control and T3 homozygous *Arabidopsis* lines expressing SbMATE using the CaMV 35S promoter. SbMATE was expressed in the Columbia ecotype (Col: non-transgenic; Col-TG: transgenic lines expressing SbMATE) and in a very Al sensitive AtALMT knock-out line (KO: non-transgenic knock-out line; KO-TG: transgenic knock out lines expressing SbMATE). Scale bar, 1 cm. FIG. 6*b* depicts Al tolerance as measured by % relative net root growth (% RNRG) in eight independent KO-TG lines. The data are the means ±s.d. (n=20). FIG. 6*c* shows the relationship between the level of SbMATE expression and Al tolerance (% RNRG) in control and selected T3 transgenic lines. FIG. 6*d* depicts root malate and citrate exudation under +/−Al conditions for control and selected T3 transgenic plants. For FIGS. 6*c* and 6*d*, the data are the means ±s.d. (n=20).

FIG. 8*a* depicts the map of the gene showing exons, introns and the region that was sequenced from each of the 300 members of the maize diversity panel for association genetics analysis. FIG. 8*b* depicts the linkage disequilibrium analysis of polymorphisms detected at ZmASL-49968, showing that ZmASL-49968 is associated with maize Al tolerance.

DETAILED DESCRIPTION OF THE INVENTION

This invention concerns the isolation of the SbMATE gene, a major Al tolerance gene underlying the $Alt_{SB}$ locus in sorghum, the cloning and functional analysis of the SbMATE gene in sorghum, and the transformation of *Arabidopsis* and Al-sensitive lines of sorghum, and other related cereal species, including wheat, barley, rice, and maize with the nucleic acid encoding the SbMATE protein. Using the compositions and methods of the invention, plant cells are genetically manipulated resulting in tolerance to aluminum in plant cells and tissues. The nucleic acid molecules, constructs and vectors of the invention and the methods of using them can be utilized to increase tolerance to aluminum in important food crops. The SbMATE gene is a member of the MATE (Multidrug and Toxin Efflux) family of membrane transporters and encodes a novel citrate efflux transporter that is activated by Al.

Figure 1:
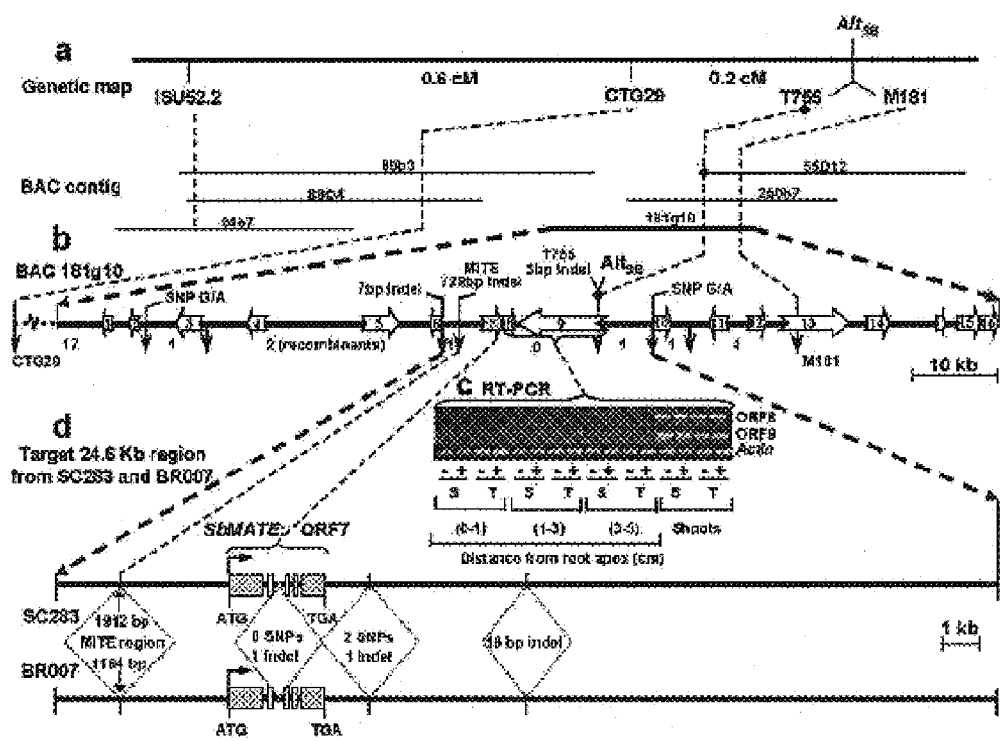
FIGS. 1a-1d depict the positional cloning of $Alt_{SB}$.

The single locus, $Alt_{SB}$, was identified as controlling Al tolerance in two different mapping populations developed from two highly Al tolerant sorghum cultivars. The major Al tolerance locus in sorghum, $Alt_{SB}$, was mapped to the terminal region of chromosome 3 in a population derived from the sorghum Al tolerance standard, SC283 (Magalhaes et al. 2004. *Genetics* 167: 1905-1914). Based on comparative mapping, it was shown that $Alt_{SB}$ is likely distinctly different from the Al tolerance locus in wheat, and hence should be represented by a novel Al tolerance gene. In our initial comparative genomic analysis of $Alt_{SB}$, markers tightly linked to $Alt_{SB}$ in our original mapping population were located near position 173 cM on the rice physical/genetic map of chromosome 1 (Magalhaes et al., supra; Jaiswal et al. 2006. *Nucl. Acids Res.* 34: D717). Based on this result, sequence-tagged site (STS) markers were developed from rice and used to evaluate a BR007 (sensitive)×SC283 (tolerant) recombinant inbred (RI) population (n=354). New STS markers were developed from sorghum genome survey sequences located within the relevant region of sorghum chromosome 3 (Klein et al. 2003. *Plant J.* 34:605-). The RIL map of $Alt_{SB}$ that included two of these STS markers, CTG29 and M181, located at 0.8 cM and completely linked to $Alt_{SB}$, respectively is shown in FIG. 1A. Our final stage of genetic mapping for the $Alt_{SB}$ region involved screening 4170 gametes from an $F_2$ population and selecting 27 recombinant individuals from the CTG29-M181 interval (See Example 2). Additional markers were developed from our sequence analysis of BAC 181g10 and used to further delimit the $Alt_{SB}$-containing interval. Two of these markers each identified a single recombination event, thus closely flanking $Alt_{SB}$. Therefore, an average recombination ratio of ~513 Kb/cm across this region allowed us to define a 24.6 Kb region that contained three predicted ORFs (ORF 7, 8, and 9), one of which had to be $Alt_{SB}$ (See FIG. 1*b*).

Sequence annotation for ORFs 8 and 9 revealed high similarity to a hypothetical protein and a sucrose phosphate synthase gene, respectively. FIG. 1*c* shows that both genes were highly expressed in shoots of near-isogenic lines (NILs) contrasting in Al tolerance but were not expressed in roots, the site where the Al tolerance mechanism must function.

Conversely, TBLASTX searches with ORF 7 identified highly similar sequences in *Arabidopsis* (At1g51340) and rice (Os01g69010) (FIG. 2a), which represent members of the multidrug and toxic compound extrusion (MATE) transporter family (Brown et al. 1999. *Mol. Biol.* 31: 393-395). MATE proteins have been implicated in the efflux of small organic molecules (Morita et al. 1998. *Antimicrob. Agents Chemother.* 42: 1778-1782; Diener et al. 2001. *Plant Cell* 13: 1625-1638; Li et al. 2002. *J. Biol. Chem.* 277: 5360-5368), which is consistent with the physiological mechanism for sorghum Al tolerance based on Al-activated root citrate exudation (Magalhaes et al., supra). Therefore, the MATE homolog isolated from *Sorghum bicolor* (here designated SbMATE) was considered the best candidate for the $Alt_{SB}$ locus and studied further.

The genomic SbMATE in sorghum is 2407 bp long. The genomic sequence for the SbMATE from the Al tolerant parent (SC283) is identified by SEQ ID NO:1 and the genomic sequence for the SbMATE from the Al sensitive parent (BR007), by SEQ ID NO:2 The full length cDNA (SEQ ID NO:3) contains 5 exons distributed over 1803 bp (FIG. 1d), which encode a 600-amino acid polypeptide (SEQ ID NO:4) with a molecular weight of ~62 kD. Sequence comparisons with the wheat Al tolerance gene, ALMT1, showed that the sorghum SbMATE is not related to the ALMT family of membrane proteins and thus is a novel tolerance gene. The topology program HMMTOP (Tusnady and Simon. 1998. *J. Mol. Biol.* 283: 489-506) predicted the SbMATE protein to contain 12 transmembrane domains (FIG. 2b) and is suggested to be localized to the plasma membrane (PSORT; Nakai and Kanehisa. 1992. *Genomics* 14: 897-911). A comparison between the SC283 (Al tolerant) and BR007 (Al sensitive) SbMATE alleles as well as for the entire 24.6 Kb region defined by high resolution mapping, showed that the SbMATE coding region is identical between the parental alleles, with polymorphisms only found within one of the introns (FIG. 1d). There were only 4 sets of polymorphisms found in the entire 24.6 Kb region with the most divergent being a large, 728 bp indel in the SbMATE promoter region at ~1.4 Kb upstream of the predicted TATA box.

Figure 3:
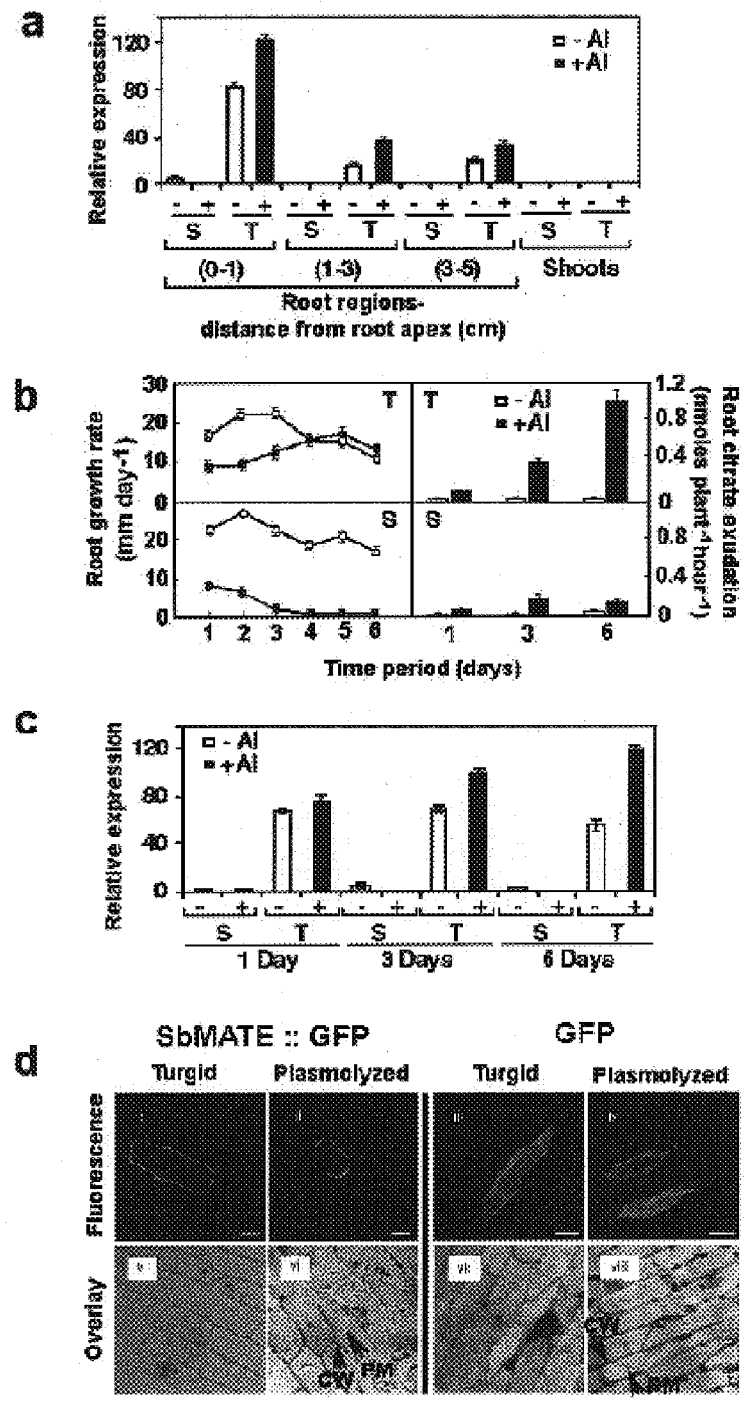
FIGS. 3a-d depict the expression and localization of SbMATE.

To verify that the sorghum MATE gene indeed is SbMATE, its expression in root tips (the site of Al tolerance and toxicity) of tolerant versus sensitive near isogenic lines (NILS) of sorghum was quantified (See Example 4). Quantitative RT-PCR analysis showed that SbMATE is expressed only in roots of the Al-tolerant NIL and that the root tip expression is Al-inducible (FIG. 3a); expression is not detectable in the root tip of the sensitive NIL. Sorghum Al tolerance is also Al-inducible over time (FIG. 3b, left panel). Al-induced inhibition of root growth decreases significantly in the tolerant NIL as root exposure time to Al increases, with inhibition of root growth decreasing from an initial inhibition of 40-50% observed on days 1 and 2 in the presence of Al, to no inhibition of root growth on days 5 and 6. This response correlates closely with the increase in Al-activated root tip citrate exudation over time of exposure to Al (FIG. 3b; right panel) and Al-induction of SbMATE expression (FIG. 3c). Exposure to Al increased SbMATE expression by 20% after one day in Al; Al inducibility increased to 40% by day 3 in Al, and by 120% by day 6. Altogether, the parallel behavior between SbMATE expression, Al tolerance and root citrate release supports our contention that the transporter is the Al tolerance locus, $Alt_{SB}$.

The subcellular localization of SbMATE was determined via transient expression of a SbMATE::GFP translational fusion protein in onion epidermal cells (See Example 7). The SbMATE protein appears to be localized to the plasma membrane (FIG. 3d), which is consistent with its proposed role in citrate efflux from root cells. Thus, these findings indicate that our candidate MATE gene for the $Alt_{SB}$ locus encodes a root citrate efflux transporter that is Al-inducible at the level of gene transcription and is also Al-activated at the level of protein function.

SbMATE expression was also examined in a 12 member sorghum diversity panel from diverse geographical origins and included BR007, the Al sensitive parent and SC283, the Al tolerant parent. The wide range of Al tolerance and sensitivity exhibited by this panel is due to an allelic series at the $Alt_{SB}$ locus (Caniato et al., supra). Differences in SbMATE expression explained most, i.e., 96%, of the phenotypic variation for Al tolerance in this panel ($r^2$=0.96, FIG. 4a). These results provide further evidence that SbMATE underlies $Alt_{SB}$ and strongly suggests that differences in gene expression constitute the basis for allelic variation at $Alt_{SB}$. Significant correlation was similarly found between SbMATE expression and Al-activated root tip citrate release (FIG. 4b), and between citrate release and Al tolerance (FIG. 4c), indicating that differences in gene expression condition the Al tolerance phenotype primarily by modulating root citrate exudation.

Figure 4:
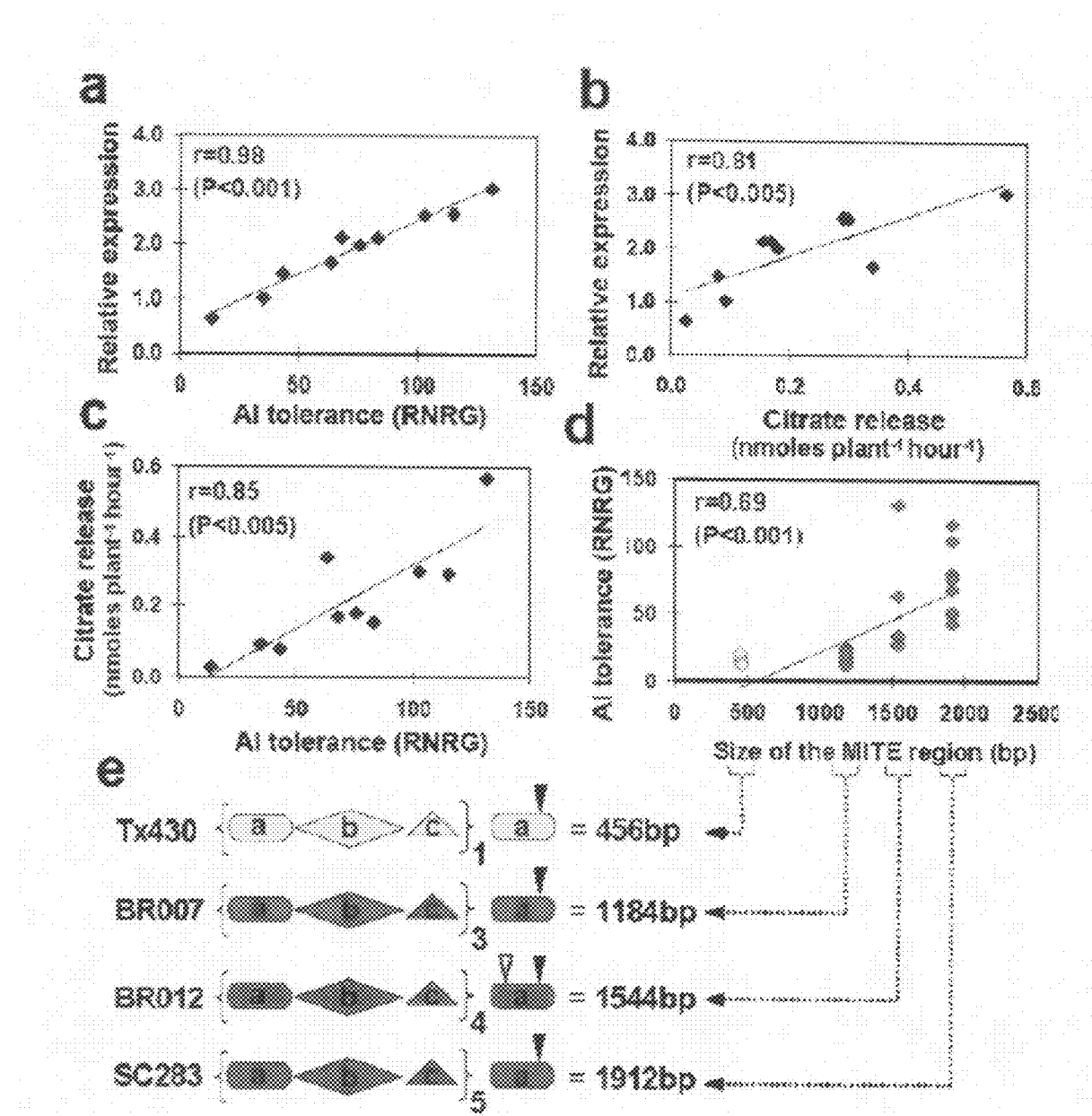
FIGS. 4a-e show the correlation of SbMATE expression, root citrate exudation and Al tolerance in 10 sorghum lines that harbor an allelic series at $Alt_{SB}$ (BR012, BR007, IS8577, SC549, 3DX, SC175, 9DX, CMS225, SC283, SC566; Caniato et al. 2007. Theor. Appl. Genet. 114: 863-76) exposed to {27} μM $Al^{3+}$ in nutrient solution.
Figure 5:
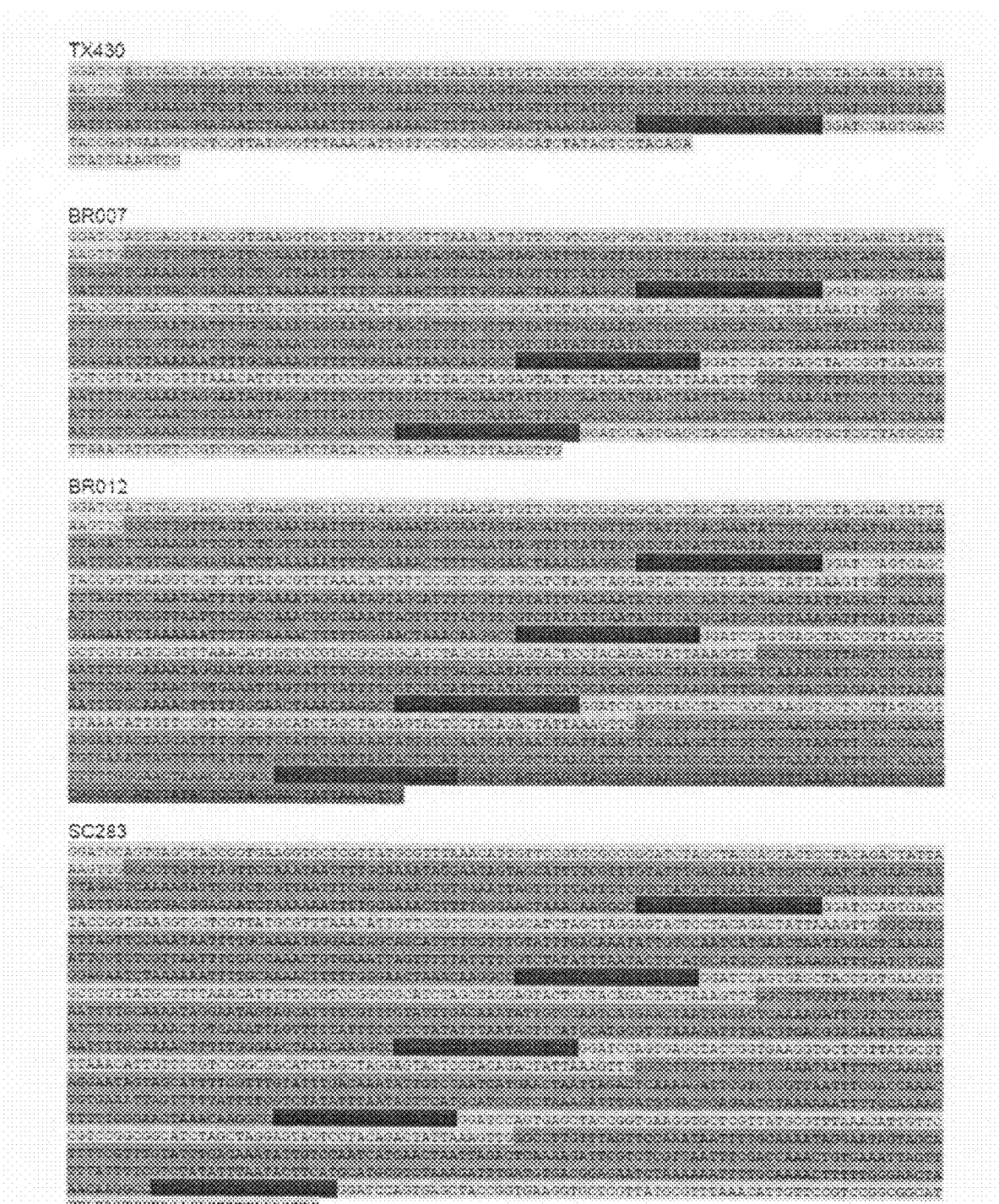
FIG. 5 shows the nucleotide sequence of the MITE-containing region in the promoter of SbMATE for the four sorghum accessions presented in FIG. 4 as representative of the four size classes for this region. As depicted in FIG. 4, the MITE-containing regions contain 3 repeating elements: a 100-bp element highlighted in yellow and labeled as (a) in FIG. 4; the 243-bp MITE insertion highlighted in blue and labeled (b) in FIG. 4; and a 21-bp element following the MITE insertion highlighted in pink and labeled (c) in FIG. 4. Each of the MITE-containing regions ends with an imperfect (a) element that contains either an 8-bp deletion, highlighted in grey, or a 12-bp deletion, highlighted in green. Note that as the MITE-containing region increases in size, the number of a-b-c repeats increases from 1 in TX430 (SEQ ID NO:5), to 3, 4 and 5 in BR007 (SEQ ID NO:6), BR012 (SEQ ID NO:7), and SC283 (SEQ ID NO:8), respectively.

The large polymorphic region upstream of the SbMATE start codon (see FIG. 1d) was amplified via PCR in an expanded sorghum panel and the size variation for this polymorphic region was found to be significantly and positively correlated with Al tolerance (FIG. 4d). This variable region was sequenced from genotypes representing the four size classes for this region (FIG. 4d) and analysis of the sequence data indicated this region was highly structured and repeated. As shown in FIG. 4e, this region is composed of an initial 100 bp sorghum sequence (unit a in FIG. 4e), followed by a larger, 243 bp sequence (unit b), that is a Tourist-like miniature inverted repeat transposable element or MITE (Bureau and Wessler. 1992. *Plant Cell* 4: 1283-1294; Wessler et al. 1995. *Curr. Opin. Genet. Dev.* 5: 814-821). The MITE insert is followed by a subsequent 21 bp sorghum sequence (unit c). This a-b-c structure is a singlet in the smallest, least Al tolerant example (Tx430) and is repeated between 3, 4, and 5 times in representatives from the next three size classes. The MITE-containing region for the four sorghum accessions presented in FIG. 4e as representative of the four size classes for this region were sequenced (FIG. 5). The sequence of the MITE-containing region from the least Al tolerant example (Tx430) is identified by SEQ ID NO:5. As the MITE-containing region increase in size, the number of a-b-c repeats (FIG. 4e) increases from 1 in TX430, to 3, 4, and 5 in BR007, BRO12, and SC283, respectively. The sequences of this MITE-containing region from BR007, BR012, and SC283 are identified by SEQ ID NO:6, SEQ ID NO:7, and SEQ ID NO:8, respectively. Thus, the region upstream from SbMATE is possibly involved in Al-tolerance. The endogenous promoter located in this region is Al-inducible and root specific, resulting in $Alt_{SB}$ expression in the root apex.

Figure 6:
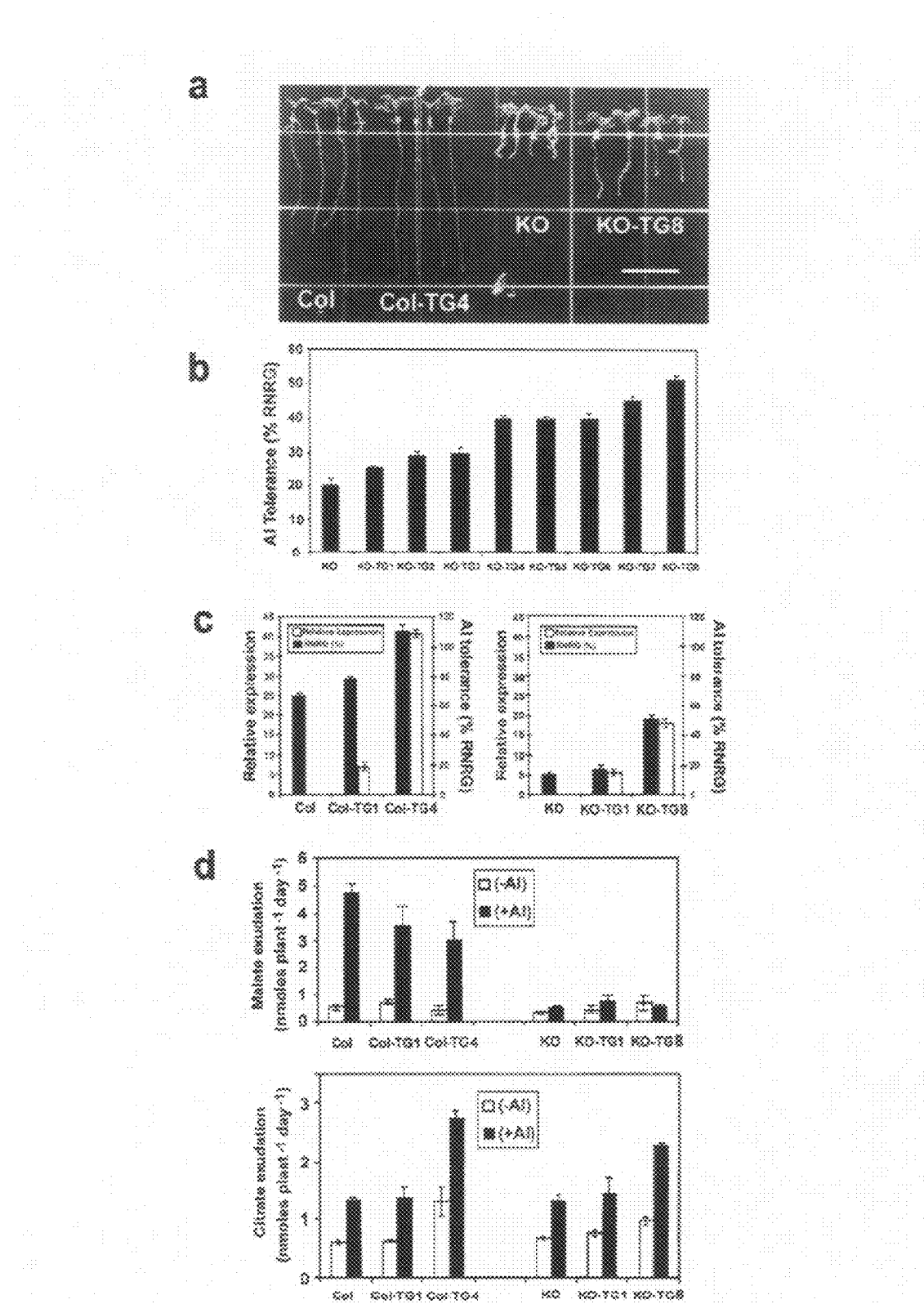
FIGS. 6a-d depict expression of SbMATE in transgenic Arabidopsis plants.
Figure 7:
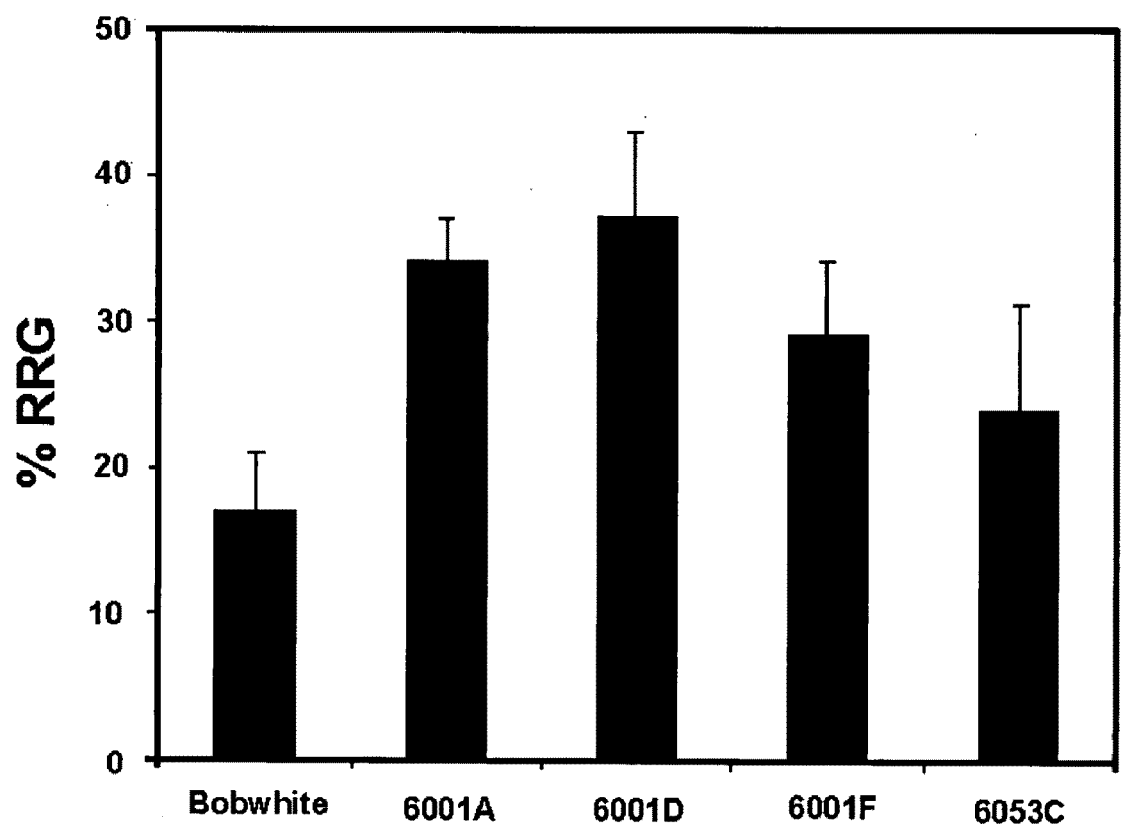
FIG. 7 depicts Al tolerance as measured by % relative root growth (% RRG). % RRG values were calculated from root growth measured over 24 hrs in +Al solution divided by root growth measured over 24 hrs in control (—Al) solution×100 for the Al sensitive wheat cultivar, Bobwhite, and four T1 transgenic Bobwhite families expressing SbMATE under the constitutive maize ubiquitin promoter. Wheat plants were grown in 0.2 mM $CaCl_2$ solution with or without 5 μM $AlCl_3$ (pH 4.5). The data are means ±S.D. (n=19 for Bobwhite; 11 for 6001A; 11 for 6001D; 8 for 6001F; and 9 for 6053).

A genetic complementation test was carried out in the *Arabidopsis thaliana* ecotype Columbia (UVT Col) and in the highly Al sensitive T-DNA knockout mutant, AtALMT1-KO, in which an *Arabidopsis* homolog of the wheat ALMT1 gene is disrupted in the first exon. We screened 10 T-DNA *Arabidopsis* insertion lines in which the 6 *Arabidopsis* genes that are the most closely related to SbMATE homologs were disrupted, and observed no reduction of Al tolerance in comparison to the Col-0 WT. This indicates that functional MATE alleles are either rare in *Arabidopsis* or not present in the Columbia ecotype. Conversely, the disruption of AtALMT1 caused a strong reduction in Al tolerance compared to WT (FIG. 6a), as the result of a lack of AtALMT1 function that leads to a nearly complete loss of Al-activated root malate efflux (Hoekenga et al., supra). Therefore, we conclude that the extremely Al sensitive AtALMT1-KO is a highly appropriate genetic background for Al tolerance complementation tests in *Arabidopsis*. Homozygous T3 lines expressing SbMATE driven by the CaMV 35S promoter were significantly more Al tolerant than control seedlings in both backgrounds (FIG. 6a). Four transgenic lines in the WT background (TG-WT) significantly outperformed the WT Columbia with regard to Al tolerance, with an average RNRG of 88±4% compared to a RNRG of 65±5% for the WT line. Expression of SbMATE in the highly Al sensitive AtALMT1 background increased the sensitivity of the complementation test, as eight transgenic lines in the KO background (TG-KO) exhibited a significant increase in Al tolerance compared to the parental line (FIG. 6b). In a separate experiment, we selected the best performing as well as a mediocre performing transgenic line in both backgrounds and found that Al tolerance increased proportionally with the level of SbMATE expression (FIG. 6c). The most tolerant transgenic lines in both backgrounds, Col-TG4 and KO-TG8, exhibited the greatest SbMATE expression and Al-activated root citrate release, but no increase in malate exudation was observed (FIG. 6d). We are generating transgenic wheat lines in the Al-sensitive cultivar, Bobwhite, where SbMATE driven by the maize ubiquitin promoter is stably expressed. In FIG. 7, the results of an experiment with T1 transgenic wheat lines shows that we have identified four transgenic lines with substantially increased Al tolerance compared to non-transgenic Bobwhite. These results with *Arabidopsis* and wheat provide experimental support that a member of the MATE family from *Sorghum bicolor*, SbMATE, is an Al-activated citrate efflux transporter that confers Al tolerance via the $Alt_{SB}$ locus.

Thus, a member of the multidrug and toxic compound extrusion 'MATE' family from *Sorghum bicolor*, SbMATE underlies the major Al tolerance locus, $Alt_{SB}$ and confers Al tolerance by an exclusion mechanism based on Al-activated citrate release from sorghum root apices. Differences in gene expression are responsible for allelic effects at $Alt_{SB}$, differences which condition both differential Al tolerance and Al-activated citrate release. Members of the complex MATE family are found in all three domains of life (Hvorup et al. 2003. *Eur. J. Biochem.* 270: 799-813) and appear to encode different phenotypes, which are largely related to their function as energy-dependent carriers of small organic molecules (Morita et al. 1998, supra; Morita et al. 2000. *J. Bacteriol.* 182: 6694-6697; He et al. 2004. *J. Bacteriol.* 186, 262-265). Searches of the TIGR database, revealed a close similarity between SbMATE and rice and *Arabidopsis* MATE members; BLASTP searches using the National Center for Biotechnology Information (NCBI) database revealed a close similarity between SbMATE, a *Medicago truncatula* multi antimicrobial extrusion protein (MatE, ABE84357.1, 1=53%, E=$2e^{-143}$), *Arabidopsis thaliana* ferric reductase defective 3 (FRD3, NP187461.1, 1=55%, E=$6e^{-138}$), and *Lupinus Albus* LaMATE (AAW30372.1, 1=51%, E=$3e^{-125}$). Additional hits with lower E values were found with the landmark of the MATE family, NorM1 (Morita et al. 1998, supra), a $Na^+$-driven $Na^+$/multidrug antiporter from the halophilic marine bacterium *Vibrio parahaemolyticus* (Morita et al. 2000, supra), an enhanced disease susceptibility 5 (EDS5) protein, and multiple hits were found for DNA-damage-inducible F-like proteins (DinF). A role for FRD3 encoding a system that mediates the efflux of an iron chelator, possibly citrate, into the xylem, thus promoting the delivery of iron to the shoot in a usable form has been proposed (Green et al. 2004. *Plant Physiol.* 136(1): 2523-2531). In proteoid (or cluster) roots of white lupin, enhanced synthesis and exudation of citrate is considered an adaptive response to mobilize phosphorous that is fixed in the soil clay fraction (Newman et al. 1998. *Planta* 208: 373-382), thus increasing phophorus (P) availability in low-P soils. Recently, a member of the MATE family, LaMATE, was found to be highly expressed in white lupin roots under P deficiency and was hypothesized to be involved with the transport of small organic molecules as a response to nutrient stress (Uhde-Stone et al. 2005. *Plant J.* 44: 840-853). Although no experimental evidence was shown supporting the involvement of either FRD3 or LaMATE as citrate carriers, extensive phylogenetic analysis with more than 70 transporter families have shown that substrate specificity is a well conserved trait that typically correlates with phylogeny, albeit exceptions have also been found (reviewed by Hvorup et al., supra). Thus, the role of SbMATE in providing Al tolerance by Al-induced citrate release suggests that the substrate from FRD3 or LaMATE is similarly citrate. Considering that both Al toxicity and P deficiency are the two most important agricultural constraints on acid soils, the MATE family appears to be critical for adaptation to these areas. However, a myriad of phenotypes such as the vacuolar sequestration of flavonoids in the seed coat endothelium (encoded by TRANSPARENT TESTA 12, Debeaujon et al., supra) and salicylic acid-dependent signaling for disease resistance (encoded by EDS5, Nawrath et al. 2002. *Plant Cell* 14: 275-286) are controlled by other family members. This, in conjunction with the hypothesis that the MATE family arose in the prokaryotic domain and that some family members were transmitted to eukaryotes (Hvorup et al., supra), suggests that Al tolerance probably originated from mutation(s) in a pre-existing and probably functional MATE family member, which provided particular characteristics that led to Al tolerance.

These data with genetically dissimilar sorghum accessions indicate that changes in gene expression are the major consequence of such mutations, and that polymorphisms within regulatory regions rather than within the coding region of the gene underlie allelic effects on Al tolerance at $Alt_{SB}$. In addition, these changes in SbMATE expression involve factors that act to drive expression specifically in sorghum root apices, which is the site that needs to be protected from Al toxicity. The candidate regulatory polymorphisms are located within the 24.6 Kb region defined by high resolution mapping, and may consist of cis-acting regulatory sequences, which could mediate sites of interaction with chromatin complexes that influence gene expression (Guo and Moose. 2003. *Plant Cell* 15: 1143-1158) or serve as binding sites to trans-acting elements such as transcription factors. Alternatively, the causal polymorphism within the target region could also encode trans-acting factors that interact with cis-acting elements. Because the two other genes in this region, ORFs 8 and 9, are not expressed in sorghum roots, this hypothesis becomes less likely. Sequence alignment between the reference alleles from SC283 and BR007 revealed that a transposon (MITE) insertion of variable size is the only polymorphic region upstream of the SbMATE translation initiation site, and size variations of this region were positively correlated with Al tolerance across an expanded sorghum panel. MITEs have been identified in the non-coding region of normal genes and have the ability to provide regulatory sequences that alter gene expression (Bureau and Wessler. 1994. *Plant Cell* 6:907-916; Wessler et al., supra; Yang et al. 2005. *Plant Cell* 17: 1559-1568). The terminal inverted repeats from a Mu transposon of maize has also been shown to contain plant cell-cycle enhancer motifs and pollen- or gamete-specific enhancer sequences (Raizada et al. 2001. *Plant J.* 25: 79-91), and a transposon insertion in the maize b locus has been identified as the mechanism providing expression specificity that yields phenotypic variants at b (Selinger and Chandler.

1999. *Proc. Natl. Acad. Sci. USA* 96: 15007-15012). The regular {abc}$_{1-5}${a} structure that gives rise to the size variations of the MITE insertion near SbMATE in different sorghum accessions raises the possibility that cis-acting elements within the repeated regions are acting multiplicatively to enhance SbMATE expression specifically in root apices. Given the monomorphic nature of the SbMATE coding region in our reference alleles, a transposon insertion may ultimately underlie Alt$_{SB}$. An example for the role of cis-acting sequences was provided for the domestication teosite branched 1 (tb1) locus, a transcriptional regulator that controls apical dominance in maize (Doebley et al. 1997. *Nature* 386: 485-488). It has recently been found that cis-acting elements away from tb1 may constitute the basis of the QTL by modulating tb1 expression (Clark et al. 2006. *Nat. Genet.* 38: 594-597). However, across our sorghum panel, linkage disequilibrium, which can be extensive in self-pollinating species such as sorghum as compared to outcrossing species (Hamblin et al. 2004. *Genetics* 167: 471-483; Hamblin et al. 2005. *Genetics* 171: 1247-1256), could cause the MITE insertion to be associated to the polymorphisms found within one of the SbMATE introns or the polymorphisms downstream of the gene stop codon. Differences in gene expression may be conditioned by the intronic polymorphisms (see, for one such example, Jeon et al. 2000. *Plant Physiol* 22: 561-570), by the additional polymorphisms downstream of the gene stop codon or by an interaction among those. An extensive association mapping effort with a highly diverse and large sorghum panel within the Alt$_{SB}$ target region is now being conducted to aid in defining the nature of the causative polymorphisms that affect SbMATE expression.

Our previous comparative mapping studies indicated that the major Al tolerance loci, Alt$_{SB}$ in sorghum and Alt$_{BH}$ in wheat, are located in non-conserved positions and are probably distinct, whereas we hypothesized that a major Al tolerance QTL that has been repeatedly detected on rice chromosome 1 is orthologous to Alt$_{SB}$ (Magalhaes et al., supra). Comparative sequence analysis between the sorghum BAC 181g10 that harbors SbMATE revealed a high degree of conservation in gene order and content with rice BAC AP003437, which is thus likely to be the rice homologue of 181g10. The best BLASTP hit that was found in the NCBI database using SbMATE as query was BAD87624 (I=76%, E=0.0), which is thus a likely rice ortholog of SbMATE that is located on AP003437. The major rice Al tolerance QTL on chromosome 1 is linked to the wheat genomic RFLP Xwg110 (Nguyen et al. 2001. *Theor. Appl. Genet.* 102: 1002-1010), which was found by sequence similarity analysis to be located to the contiguous rice BACs AP003433/AP003451 at position ~158 cM on rice chromosome 1 (I=78%, E=6.2 e$^{-14}$). The target rice BAC defined by the comparative genomics approach we have used to positionally clone SbMATE in sorghum, AP003437, is contiguous to AP003451 at position 159 cM. These results provide further, sequenced-based support for our comparative mapping hypothesis for conservation of Al tolerance genes over a long evolutionary continuum, between the Oryzeae (rice) and Andropogoneae (maize and sorghum) tribes within the grass family (Magalhaes et al., supra).

Possible homologs of the sorghum SbMATE in maize were identified using recursive searches. Sorghum SbMATE was used to query the rice genome using TBLASTN at Gramene and seven putative homologs to SbMATE were identified. The maize MAGI GSS database was then queried with the sorghum SbMATE and also with sequences from the seven rice SbMATE-like genes. The maize MATE with the closest sequence similarity to or sorghum MATE, designated ZmASL49968 (for *Zea mays* Alt$_{SB}$-like gene) was chosen for further analysis. This gene shared 64% identity and 73% similarity with the sorghum SbMATE gene at the amino acid level. Two lines of investigation are utilized to identify genes and processes important for Al tolerance. The first, utilizing association analysis, a statistical genetic approach, to correlate particular nucleotide polymorphisms with significant differences in Al tolerance between inbred lines. This analysis is subsequently followed by linkage analysis in selected F2 populations in order to further verify associations found with Al tolerance. Three datasets are required for association analysis: 1) trait data, 2) genotype data, and 3) sufficient marker data from across the genome of the study population, in order to evaluate true positive from false positive results (those due to population structure or kinship). We have phenotyped a 288 maize inbred line association panel assembled by Dr. Ed Buckler, USDA-ARS, Cornell University, using our standard hydroponic methodologies for quantifying root growth under +/−Al conditions. Based on five repeated experiments, the estimate for the heritability of net seminal root growth (the amount of root growth that occurs during a 2-day stress treatment) is 0.65. We are using the latest form of mixed model ANOVA; this model was developed by Dr. Ed Buckler and has been recently published in *Nature Genetics* (2006. 38:203-208). We are employing a set of 500 SNP from across the maize genome to empirically calculate the significance threshold for Al tolerance.

Figure 8A:
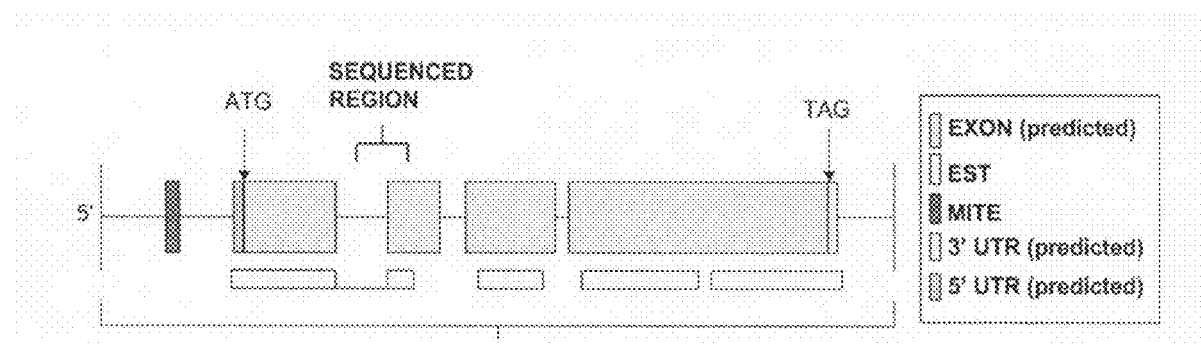
FIGS. 8*a-b* show that ZmASL-49968 is a homolog of SbMATE in sorghum and is a candidate maize Al tolerance gene.
Figure 8B:
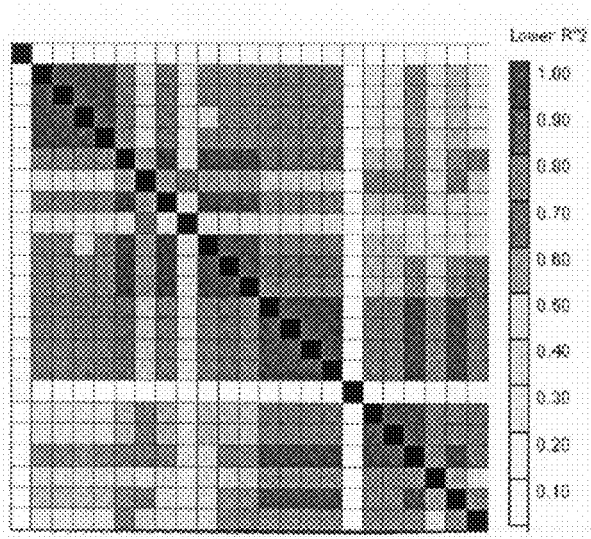
Figure 9:
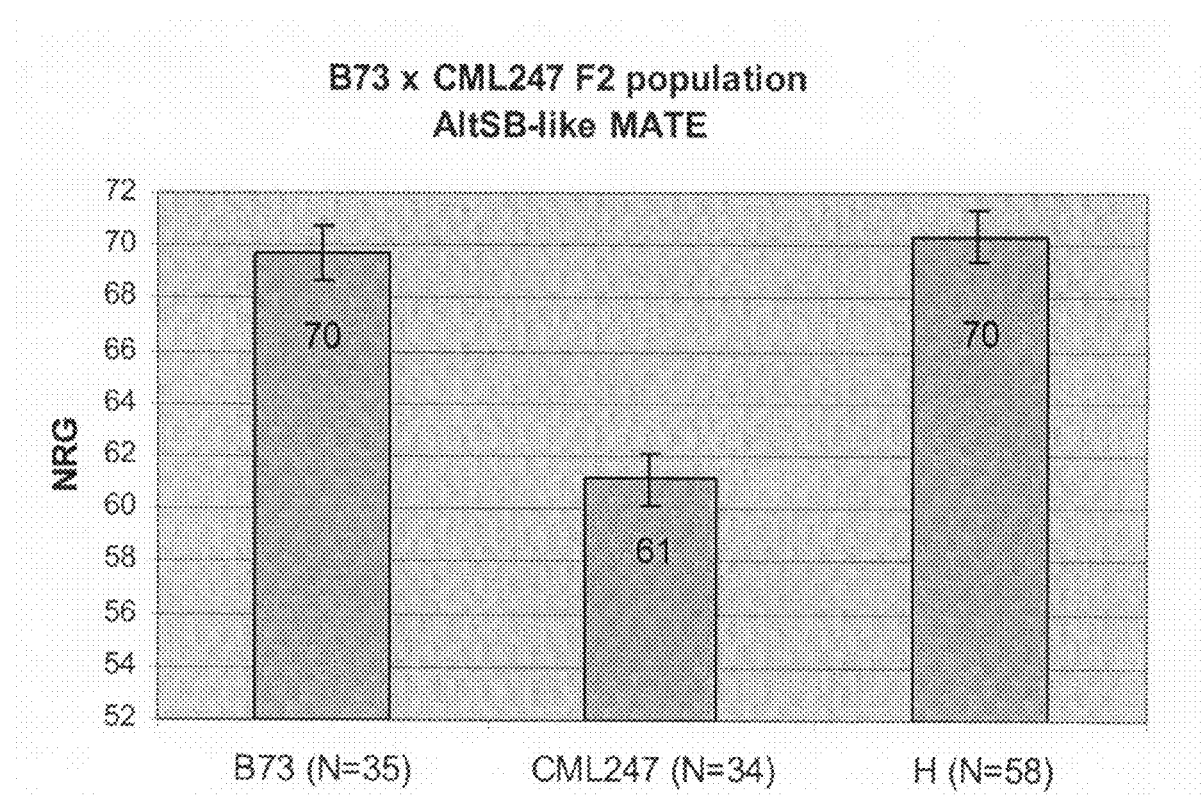
FIG. 9 depicts the linkage analysis in the B73×CML247 $F_2$ population and confirms the association analysis of ZmASL-49968. ANOVA for ZmASL-49968: F=8.44, p=0.004. The maize parent, B73, harbors the superior allele for ZmASL-49968 and CML247 harbors the inferior allele as predicted by association analysis. The F2 progeny from the cross of B73× CML247 that are either homozygous or heterozygous for the superior B73 allele are considerably more Al tolerant than those homozygous for the inferior, CML247 allele. This is seen as net root growth (NRG) for F2s harboring the superior allele was 70 mm in 39 uM $Al^{3+}$, while NRG for F2's harboring the inferior allele was only 61 mm.

We then sequenced the region of ZmASL-49968 depicted in FIG. 8a in all 288 of the inbred lines in the maize association panel. Statistical analysis indicates that polymorphisms in this gene are significantly associated with maize Al tolerance, strongly suggesting this is a candidate Al tolerance gene. The details of the association analysis for this gene are depicted in FIG. 8b. The significance of this gene in maize Al tolerance was then verified with a linkage population, using an F2 cross between parents known to differ in the alleles detected for ZMASL-49968 (B73×CML247). As seen in FIG. 9, the superior allele of ZmASL-49968 carried by the B73 variety is completely dominant to the sensitive allele carried by CML247.

Figure 10:
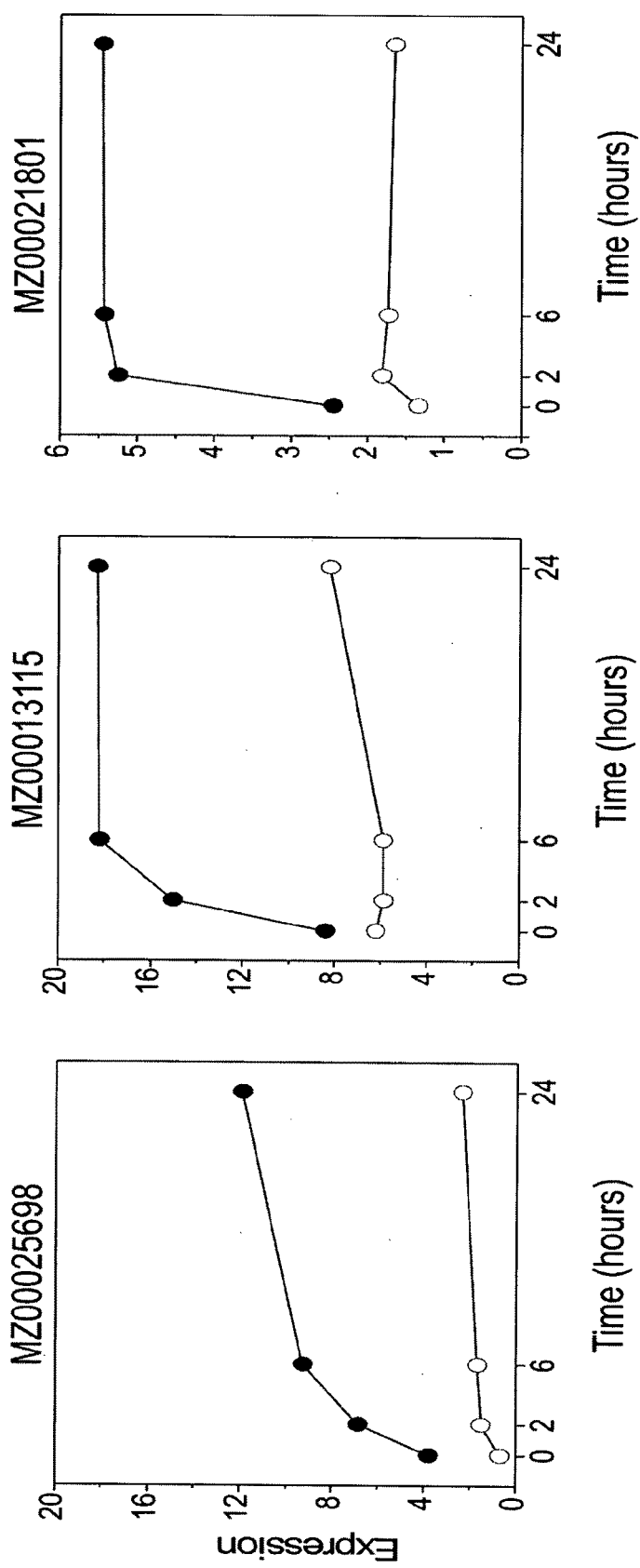
FIG. 10 depicts expression profiles of array features representing MATE-like genes up regulated by Al treatment (at 20% FDR). Gene expression levels are represented by their estimated least-square means, in genotype (●) C100-6, Al-tolerant and (○) L53, Al-sensitive. Note the Y-axis (expression) scale varies between plots.
Figure 11:
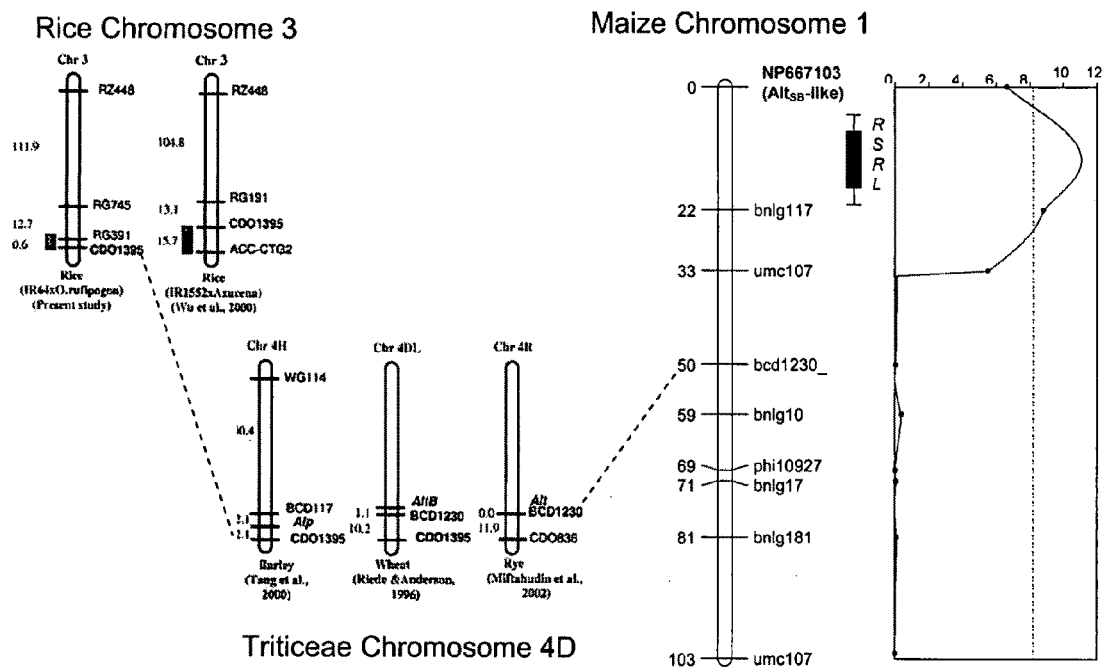
FIG. 11 depicts the comparative mapping of maize, rice and wheat QTL with a second maize homolog of SbMATE that is also a candidate maize Al tolerance gene. A region of maize chromosome 1 contains the MATE clone that is a homolog of SbMATE and was derived from EST NP667103. A QTL in the Embrapa recombinant inbred line mapping population is also located in this region of maize chromosome 1 and explains 13.7% of the variation in Al tolerance. The RFLP probes bcd1230 and cdo1395 can be used as anchor markers between the maize, rice and wheat genomes, suggesting putative orthologous regions between maize, rice and Triticeae that harbor Al tolerance genes or QTL.
Figure 12:
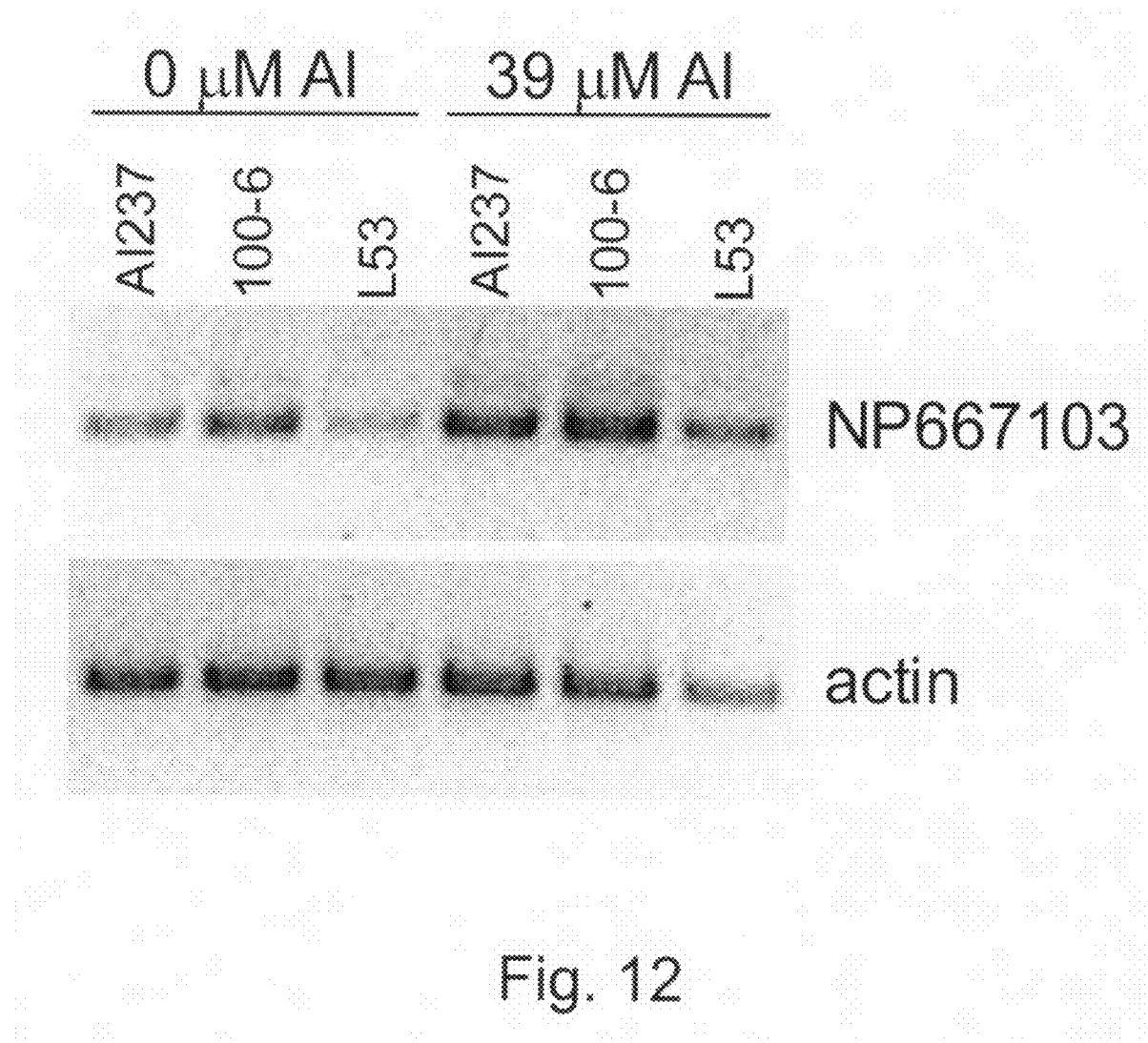
FIG. 12 depicts expression analysis of NP667103. Semi quantitative RT-PCR-based analysis of expression for NP667103 and actin (loading control) was determined using total RNA extracted from roots of Al237 (Al-tolerant parent of Embrapa RIL population), C100-6 (a second Al-tolerant maize line, used in microarray experiments) and L53 (Al-sensitive maize line, used in microarray experiment and Al-sensitive parent of Embrapa RIL population) treated with 0 or 39 μM $Al^{3+}$ for 24 hours.

Microarray analysis was used to examine global gene expression profiling in the maize root tip of Al tolerant and sensitive maize genotypes. We identified a second candidate maize Al tolerance gene as a homolog of SbMATE in sorghum. As seen in FIG. 10, we found three genes in the maize root tip whose expression were strongly induced by Al only in the root tip of the tolerant maize lien and also showed higher constitutive (—Al) expression in the tolerant line. One of these, MZ000025698 in FIG. 10, was derived from EST NP667103 and is closest in sequence to the sorghum SbMATE for the 3 Al-inducible MATE genes in maize (53% identical at the amino acid level) and was chosen for further study. Markers were derived for a region of this gene and mapped on the Embrapa Recombinant Inbred line population derived from the cross between an Al tolerant×sensitive parent. As seen in FIG. 11, this gene maps to a major Al tolerance QTL previously identified by Embrapa Maize and Sorghum using this population. Finally, we confirmed the microarray results with RT-PCR analysis of expression of this gene in the root tips of two Al tolerant maize lines, Al237 and Cat100-6 and the Al sensitive line, L53. Al237 and L53 are the parents of the Embrapa RIL mapping population. As seen in FIG. 12, the gene is expressed much more strongly in the root tips of the 2 tolerant lines, both in the absence and presence of Al.

The ALMT1 gene cloned by Sasaki and coworkers (Sasaki et al., supra) is an Al-activated malate transporter that does not belong to any existing protein family of known function. Direct sequence alignment between wheat ALMT1 and sorghum SbMATE has confirmed that these genes are distinct. It is however interesting that SbMATE and ALMT1, two non-orthologous genes, evolved independently to encode analogous but not identical physiological mechanism of Al exclusion from root apices based on organic acid release. Breeding strategies can be designed to take advantage of the additive effects provided by non-orthologous Al tolerance genes that control convergent physiological mechanisms of Al tolerance.

In a preferred embodiment of the present invention, the nucleic acid encoding an Al-tolerance gene is selected from the group consisting of: (a) an isolated DNA encoding an Al-inducible citrate efflux transporter; (b) an isolated DNA which hybridizes to isolated DNA of (a) above and which encodes an Al-inducible citrate efflux transporter protein or a peptide having an Al-inducible citrate efflux transporter biological activity; and (c) an isolated DNA differing from the isolated DNAs of (a) and (b) above in nucleotide sequence due to the degeneracy of the genetic code, and which encodes an Al-inducible citrate efflux transporter protein or a peptide having an Al-inducible citrate efflux transporter biological activity. "DNA which hybridizes to isolated DNA" refers to DNA sequences that can be identified in a Southern hybridization experiment under stringent conditions as is known in the art (see, for example, Sambrook et al. 1989. Molecular Cloning: A Laboratory Manual, Second Edition, Cold Spring Harbor Laboratory Press, Cold Spring Harbor, N.Y.). This includes homologs from other species that show up to 80% sequence identity with the sorghum Al tolerance gene.

In the most particularly preferred embodiment of the present invention, the nucleic acid encoding an Al-inducible citrate efflux transporter gene is the SbMATE gene having the sequence identified by SEQ ID NO:3 or a portion thereof having Al-inducible citrate efflux transporter biological activity.

In a further embodiment of the present invention, said DNA is a recombinant chimeric gene construct comprising a promoter operable in a plant cell and a DNA encoding the Al-inducible citrate efflux transporter described above. Said promoter can be a root specific, Al-inducible-promoter. In another embodiment, the chimeric gene construct additionally encodes at least one selectable marker and/or further comprises a heterologous coding sequence, wherein the heterologous coding sequence is an isolated DNA encoding a polypeptide sequence having a property which is advantageous to the plant and which is different from the Al-inducible citrate efflux transporter. Genes encoding polypeptides having properties advantageous to the plant and anti-phytopathogenic polypeptides are well known in the art. Examples include genes which encode proteins which protect plants against pathogens, herbicides, fungicides, insecticides, or disadvantageous environmental influences, wherein the disadvantageous environmental influences comprise heat, cold, wind, unfavorable soil conditions, moisture and dryness.

In a still further preferred embodiment of the present invention, said recombinant chimeric gene construct further comprises DNA encoding a 5' untranslated region containing a translational enhancer and DNA encoding a 3' untranslated region containing a functional polyadenylation signal, or other regulatory sequences present 5' of the SbMATE translation initiation codon up to the 7 bp indel genetic marker, or 3' of the SbMATE translation termination codon up to the SNP G/A genetic marker, or parts of these regulatory elements.

In another preferred embodiment of the present invention, the DNA sequence encoding the protein or peptide having Al-inducible citrate efflux transporter activity or the DNA sequence comprising the heterologous coding sequence is derived from a mammalian gene, a plant gene or a microorganism gene or is a synthetic gene.

In a preferred embodiment of the present invention said DNA is contained in a vector under the control of a promoter allowing its expression in said transgenic plant. Further embodiments of the invention include plant cells transformed by these vectors, plant parts, and plants and their progeny containing the chimeric genes.

In a preferred embodiment of the present invention, a host cell containing the DNA of the invention is a bacterial cell, in particular, an *Agrobacterium tumefaciens* cell.

In a preferred embodiment of the present invention, the protein encoded by said DNA sequence is an Al-inducible citrate efflux transporter. In a particularly preferred embodiment of the present invention, said transporter is an Al-inducible citrate efflux transporter from *Sorghum bicolor*, SbMATE, identified by SEQ ID NO:4.

Still another embodiment of this invention is the method of making a recombinant Al-tolerant plant, said method comprising: providing a plant cell capable of regeneration; transforming said plant cell with a DNA segment encoding an Al-inducible citrate efflux transporter, where said DNA segment is selected from the group consisting of: (a) an isolated DNA encoding an Al-inducible citrate efflux transporter; (b) an isolated DNA which hybridizes to isolated DNA of (a) above and which encodes an Al-inducible citrate efflux transporter protein or a peptide having an Al-inducible citrate efflux transporter biological activity; and (c) an isolated DNA differing from the isolated DNAs of (a) and (b) above in nucleotide sequence due to the degeneracy of the genetic code, and which encode an Al-inducible citrate efflux transporter protein or a peptide having an Al-inducible citrate efflux transporter biological activity; and then regenerating a recombinant Al-tolerant plant from said transformed plant cell.

Yet another embodiment of this invention is the method of making a recombinant Al-tolerant plant, said method comprising: providing a plant cell capable of regeneration; transforming said plant cell with the chimeric gene construct comprising a promoter operable in said plant cell, and a DNA segment encoding an Al-inducible citrate efflux transporter, where said DNA segment is selected from the group consisting of: (a) an isolated DNA encoding an Al-inducible citrate efflux transporter; (b) an isolated DNA which hybridizes to isolated DNA of (a) above and which encodes an Al-inducible citrate efflux transporter protein or a peptide having an Al-inducible citrate efflux transporter biological activity; and (c) an isolated DNA differing from the isolated DNAs of (a) and (b) above in nucleotide sequence due to the degeneracy of the genetic code, and which encode an Al-inducible citrate efflux transporter protein or a peptide having an Al-inducible citrate efflux transporter biological activity; and then regenerating a recombinant Al-tolerant plant from said transformed plant cell.

A further embodiment of the present invention is a method for the production of a transgenic plant displaying tolerance to aluminum comprising the introduction of a genetically engineered DNA sequence encoding at least one peptide having an Al-inducible citrate efflux transporter activity, into the genetic material of a suitable plant. The term "genetic material" refers to the nuclear genome of a plant cell, an organelle genome of the plant cell or an extrachromosomal form. The term "introduction" refers to a method which is capable of introducing said genetically engineered DNA sequence into said genetic material of a plant cell. Preferred examples of said method are *Agrobacterium*-mediated transfer, plant virus mediated-transfer, microinjection, microprojectile bombardment, electroporation, PEG-mediated transformation and transformation of plant protoplasts with virus-based stable vectors, all methods well known and practiced in the art. In a further preferred embodiment of the present invention said introduction is carried out by transfection using the *Agrobacterium* system.

It is yet another embodiment of the invention to provide methods for the manipulation of Al-inducible citrate efflux transporter gene sequences for their expression in transgenic plants, both monocotyledoneous and dicotyledoneous plants. In a preferred embodiment of the present invention the transgenic plant is cotton, maize, peanut, sunflower, tobacco, rice, wheat, rye, barley, alfalfa, tomato, cucumber, soya, sweet potato, grapes, rapeseed, sugar beet, tea, strawberry, rose, chrysanthemum, poplar, eggplant, sweet pepper, walnut, pistachio, mango, banana, or potato. In a particularly preferred embodiment of the invention, SbMATE is expressed in sorghum. The transgenic plants thus modified have enhanced tolerance to aluminum.

The genes for an Al-inducible citrate efflux transporter of this invention are expressed in transgenic plants thus causing the biosynthesis of an Al-inducible citrate efflux transporter in the transgenic plants. In this way transgenic plants with enhanced tolerance to aluminum are generated. For their optimal expression in transgenic plants, the Al-inducible citrate efflux transporter gene and adjacent sequences may require modification and optimization.

The preferred an Al-inducible citrate efflux transporter biosynthetic genes may be unmodified genes, should these be expressed at high levels in target transgenic plant species, or alternatively may be genes modified by the removal of destabilization and inappropriate polyadenylation motifs and illegitimate splice sites, and further modified by the incorporation of plant preferred codons, and further with a GC content preferred for expression in plants. Although preferred gene sequences may be adequately expressed in both monocotyledonous and dicotyledonous plant species, sequences can be modified to account for the specific codon preferences and GC content preferences of monocotyledons or dicotyledons.

Transgenic plants can be transformed with a DNA segment encoding an Al-inducible citrate efflux transporter in the absence of an exogenously provided promoter. However, when chimeric gene constructs comprising a promoter operable in said plant cell and a DNA segment encoding an Al-inducible citrate efflux transporter are utilized for the transformation, optimal expression of an Al-inducible citrate efflux transporter results. The expression of Al-inducible citrate efflux transporter genes in transgenic plants is behind a promoter shown to be functional in plants. The choice of promoter will vary depending on the temporal and spatial requirements for expression, and also depending on the target tissue or species. The expression of Al-inducible citrate efflux transporter genes in transgenic plants can be under the regulation of promoters which are constitutive or promoters which are regulated. Such promoters are well known in the art and described, for example, in U.S. Pat. No. 5,589,625; examples are: cauliflower mosaic virus 35S-promoter, rice actin promoter, rbc S promoter from different species, Agrobacter TR2' promoter, phaseolin gene promoter or the NOS promoter. Preferred promoters which are expressed constitutively include CaMV 35S, the cauliflower mosaic virus 35S-promoter, and 19S promoters, and promoters from genes encoding actin or ubiquitin. Constitutive expression of the Al-inducible citrate efflux transporter SbMATE under the control of the cauliflower mosaic virus 35S-promoter or the ubiquitin promoter is preferred.

The expression of the SbMATE genes of this invention can also be controlled, i.e., under the regulation of promoters which are regulated. Thus, this transformation method can be developed to provide Al tolerance to particular crops at specific times during the crop plant's life cycle or in particular parts of the plant, such as is seen with the endogenous promoter of the invention which is found upstream of SbMATE and is root-specific and Al-inducible. An advantage of controlled expression of the chimeric gene construct is that SbMATE is expressed only at the appropriate time and/or to the appropriate extent and/or only in particular parts of the plant. A further advantage is that parts of plants that are inaccessible to conventional protective measures, can be protected using this method either through constitutive expression of the nucleic acid in all tissues or through tissue-specific expression of the nucleic acid as controlled by tissue or stage-specific promoters. Furthermore, this transformation method to control tolerance to aluminum and these transgenic plants can be further developed to where expression of the gene occurs under particular circumstances, e.g., wounding, drought, and chemical induction.

In addition to the selection of a suitable promoter, constructions for SbMATE expression in plants require an appropriate transcription terminator to be attached downstream of the heterologous SbMATE gene. Several such terminators are available and known in the art (e.g. tml from CaMV, E9 from rbcS). Any available terminator known to function in plants can be used in the context of this invention.

Numerous other sequences can be incorporated into expression cassettes for SbMATE genes. These include sequences which have been shown to enhance expression such as intron sequences (e.g. from Adhl and bronzel) and viral leader sequences (e.g. from TMV, MCMV and AMV).

For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. 1986. *Biotechnology* 4: 1093-1096). For both direct gene transfer and *Agrobacterium*-mediated transfer, transformation is usually (but not necessarily) undertaken with a selectable marker which may provide resistance to an antibiotic (kanamycin, hygromycin or methatrexate) or a herbicide (sulfonylurea, imidazolinone, or basta). The choice of selectable marker is not, however, critical to the invention.

An additional embodiment of the invention relates to peptides which have Al-inducible citrate efflux transporter activity which can be used to generate antibodies. Such antibodies can be used to detect the presence a peptide having Al-inducible citrate efflux transporter biological activity in biological samples.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, here the SbMATE protein, operably linked to a promoter and/or other regulatory sequences.

As used herein, the term "express" or "expression" is defined to mean transcription alone. The regulatory elements are operably linked to the coding sequence of the SbMATE gene such that the regulatory element is capable of controlling expression of SbMATE gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, as for example, the promoter disclosed here which specifically induces the SbMATE gene expression in root apices, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence (described above) which specifically induces the SbMATE gene expression in root tips. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posftranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Kienow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to SbMATE polypeptide that is substantially free of other proteins, lipids, carbohydrates or other materials with which it is naturally associated. One skilled in the art can purify SbMATE using standard techniques for protein purification. The purity of the SbMATE polypeptide can also be determined by amino-terminal amino acid sequence analysis.

The invention includes functional SbMATE polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of SbMATE polypeptide", refers to all fragments of SbMATE that retain SbMATE activity and function in the aluminum tolerance pathway. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of SbMATE in the aluminum tolerance pathway can be utilized in bioassays to identify functional fragments of SbMATE polypeptide or related polypeptides. Thus, two orthologs of SbMATE in maize having between 53% to 64% identity and 73% to 75% similarity at the amino acid level to the sorghum SbMATE gene have been found in Al tolerant maize lines, and the gene encoding these polypeptides is preferentially expressed in the root tips of Al-tolerant plants in an Al-inducible manner, indicating that these orthologs harbor a portion of the SbMATE polypeptide that indeed has SbMATE biological activity.

Modifications of the SbMATE primary amino acid sequence may result in further mutant or variant proteins having substantially equivalent activity to the SbMATE polypeptides described herein. Such modifications may be deliberate, as by site-directed mutagenesis, or may occur by spontaneous changes in amino acid sequences where these changes produce modified polypeptides having substantially equivalent activity to the SbMATE polypeptides. Any polypeptides produced by minor modifications of the SbMATE primary amino acid sequence are included herein as long as the biological activity of SbMATE is present; e.g., having a role in pathways leading to aluminum tolerance in plants.

A heterologous coding sequence refers to coding sequences which encode peptides or proteins, unrelated to, or, other than, the SbMATE polypeptides provided above and which are not intrinsically found in the position provided in the chimeric gene construct.

Genes encoding a SbMATE protein can be cloned using a variety of techniques according to the invention. The simplest procedure for the cloning of SbMATE genes requires the cloning of genomic DNA from an organism identified as producing a SbMATE protein, and the transfer of the cloned DNA on a suitable plasmid or vector to a host organism which does not produce the SbMATE protein, followed by the identification of transformed hosts to which the ability to produce the SbMATE protein has been conferred. The transforming SbMATE-conferring DNA can be cleaved into smaller fragments and the smallest which maintains the SbMATE-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a SbMATE polypeptide and which hybridize under stringent conditions to the SbMATE sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Unless otherwise indicated, sequence alignments and percent identity calculations were performed using the Megalign program of the LASERGENE bioinformatics computing suite (DNASTAR Inc., Madison, Wis.), or any equivalent program. Multiple alignment of the sequences was performed using the Clustal W method of alignment (Higgins and Sharp (1989. *CABIOS* 5:151-153) with the default parameters (GAP PENALTY=10, GAP LENGTH PENALTY=1.0), while default parameters for pairwise alignments using the Clustal W method were GAP PENALTY=10, GAP LENGTH PENALTY=1.0, Slow-Accurate unless otherwise indicated.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence, sorghum. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have SbMATE-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the SbMATE polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they continue to possess the desired biological activity of the native protein, that is, SbMATE-like activity as described herein. Such variants may result from, for example, genetic polymorphism or from human manipulation. Biologically active variants of a native SbMATE protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even one amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired SbMATE activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of SbMATE protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful cloning of SbMATE is a major step in our understanding of the regulatory mechanisms underlying aluminum tolerance in plants. Deciphering the mechanism by which this gene functions to result in root growth in the presence of high levels of aluminum will aid in devising new strategies and/or control points for improving aluminum tolerance in crops.

EXAMPLES

Having now generally described this invention, the same will be better understood by reference to certain specific examples, which are included herein only to further illustrate the invention and are not intended to limit the scope of the invention as defined by the claims.

Example 1

Phenotypic Analysis of Sorghum Al Tolerance

Sorghum Al tolerance based on root growth inhibition elicited by $\{27\}$ μM $Al^{3+}$ (brackets denote free $Al^{3+}$ activity) was assessed according to the methods detailed in Caniato et al., supra. Briefly, sorghum seeds were surface-sterilized with 0.5% (w/v) NaOCl for 15 min, rinsed with ultra-pure water and allowed to germinate on wet filter paper for 3 days at 26° C. Seedlings were then transplanted to 8 L tubs containing complete nutrient solution lacking Al (Magnavaca et al. 1987. In: *Genetic Aspects of Plant Mineral Nutrition*, Gabelman and Loughman (Eds.) Martinus-Nijhoff Publications, Dordrecht, Netherlands) at pH 4.0. After 24 hrs the solution was changed to either control nutrient solution (—Al) or nutrient solution containing $\{27\}$ μM $Al^{3+}$ for measurement of root growth. Two mapping populations were employed: first a set of 354 BR007XSC283 recombinant inbred lines (RIL) and then for the high resolution mapping, 2035 $F_2$ individuals from a BR007XSC283 cross. Individual RIL and $F_2$ individuals were assigned into tolerant and sensitive classes based on relative root growth (RRG) values and by scoring visual root damage caused by Al (Magalhaes et al., supra) in 14 individuals per BR007XSC283 recombinant inbred line family or for individual $F_2$ plants for the high resolution mapping population. Relative root growth values were determined as follows. After a 4-day germination period, seedlings were allowed to acclimate in control nutrient solution lacking Al for 24 hr, at which time the initial length of each seedling's root in control solution (ilc) was measured. Final lengths in control solution (flc) were recorded 24 hr later, followed by replacement of the control nutrient solution with a solution of identical composition but containing Al. Final root lengths under Al treatment (flAl) were obtained after 5 days of exposure to Al. The degree of root growth inhibition caused by Al over the 5 day exposure period relative to the control root growth was calculated as RRG (% relative root growth)=$[(flAl-flc)_{5d}/(flc-ilc)_{1d}\times 5]\times 100$.

SbMATE genotypes for the 27 $F_2$ recombinants identified by high resolution mapping were assigned by progeny testing of 21 individuals per $F_{2:3}$-derived family in each of two separate experiments. Relative net root growth (RNRG) means for the sorghum lines BR012, BR007, IS8577, SC549, 3DX, SC175, 9DX, CMS225, SC283, SC566, which were used for the correlation analyses with SbMATE, expression, citrate release and size of the MITE insertion region, are those shown in Table 1 here and in Caniato et al., supra. RNRG values were determined based on growing the individuals from each $F_{2:3}$-derived family in either control (—Al) nutrient solution or the same nutrient solution plus Al. After 5 days of root growth in the +/−Al solutions, root growth over that 5 day period was determined and RNRG calculated as (root growth in Al)/(control root growth)×100, thus being expressed as a percent of control root growth.

TABLE 1

Percent Relative Net Root Growth (RNRG) means and standard errors of the means for sorghum accessions subjected to $\{27\}$ μM $Al^{3+}$, $\{37\}$ μM $Al^{3+}$ and $\{58\}$ μM $Al^{3+}$ in nutrient solution.

| | | RNRG (%, mean ± standard error of the mean) | | |
|---|---|---|---|---|
| Accessions | Other Names | $\{27\}$ μM $Al^{3+}$ | $\{37\}$ μM $Al^{3+}$ | $\{58\}$ μM $Al^{3+}$ |
| *S. verticilliflorum* | | — | — | — |
| IS3620C | SC303 | 26 ± 5.1 a | — | — |
| BTx642 | B35, SC35 | 15 ± 2.2 a | — | — |
| *S. halepense* | | — | — | — |
| Tx2784 | Sudangrass | 17 ± 2.5 a | — | — |
| Tx2785 | Sudangrass | 13 ± 1.5 a | — | — |
| CMSXS912[a] | PU64294 | 15 ± 1.2 a | — | — |
| 9929020 | | 50 ± 2.5 b | — | — |
| CMSXS235[a] | 9929036 | 51 ± 9.1 b | — | — |
| SC175-14 | CMSXS190 | 83 ± 2.4 c | 60 ± 5.8 c | 29 ± 0.6 a |
| SC414-12-E[a] | | 19 ± 1.5 a | — | — |
| 9929034 | | 80 ± 1.6 c | — | — |
| IS8577 | | 43 ± 4.9 b | 34 ± 3.1 b | 12 ± 0.8 a |
| SC112-14[a] | | 42 ± 4.6 b | 20 ± 3.6 a | 8 ± 0.0 a |
| 9DX9/11[a] | | 68 ± 7.9 c | 72 ± 0.3 c | 22 ± 0.6 a |
| CMSXS153[a] | | 68 ± 13.8 c | 43 ± 0.1 b | 13 ± 4.0 a |
| V20-1-1-1[a] | | 65 ± 12.2 c | — | — |
| 5DX-61-6-2[a] | | 98 ± 9.5 d | 72 ± 0.4 c | 25 ± 2.0 a |

TABLE 1-continued

Percent Relative Net Root Growth (RNRG) means and standard errors of the means for sorghum accessions subjected to {27} μM $Al^{3+}$, {37} μM $Al^{3+}$ and {58} μM $Al^{3+}$ in nutrient solution.

| Accessions | Other Names | RNRG (%, mean ± standard error of the mean) | | |
|---|---|---|---|---|
| | | {27} μM $Al^{3+}$ | {37} μM $Al^{3+}$ | {58} μM $Al^{3+}$ |
| 3DX57/1/910[a] | | 76 ± 4.4 c | 39 ± 1.3 b | 14 ± 0.7 a |
| Brandes | BR501 | 75 ± 16.0 c | 67 ± 17.8 c | 22 ± 3.5 a |
| SC748-5[a] | CMSXS173R | 12 ± 1.1 a | — | — |
| SC549 | | 64 ± 10.3 c | 64 ± 0.4 c | 29 ± 0.1 a |
| IS10317 | CMSXS238B | 22 ± 1.5 a | — | — |
| ARG1 | | 16 ± 2.8 a | — | — |
| ATF14 | | 95 ± 5.2 d | 71 ± 2.1 c | 32 ± 4.7 a |
| SC283 | CMSXS136 | 115 ± 6.0 e | 104 ± 1.6 d | 46 ± 5.1 b |
| CMSXS226R[a] | | 129 ± 3.2 e | 134 ± 1.5 d | 46 ± 17.8 b |
| CMSXS227R[a] | | 126 ± 8.4 e | 148 ± 10.2 d | 62 ± 7.3 c |
| BR007B | CMSXS101B | 14 ± 0.7 a | — | — |
| BR001B | Wheatland | 18 ± 2.9 a | — | — |
| 9929030 | | 28 ± 1.5 a | — | — |
| CMSXS156B[a] | BTx1391 | 17 ± 1.7 a | — | — |
| BTx623 | BR009 | 23 ± 2.4 a | — | — |
| BTx643 | B1 | 13 ± 1.3 a | — | — |
| IS10662 | CMSXS237B | 16 ± 1.1 a | — | — |
| BTx644 | B807 | 12 ± 1.5 a | — | — |
| BR012R[a] | CMSXS178R | 35 ± 4.0 b | — | — |
| CMSXS182R[a] | | 46 ± 3.0 b | — | — |
| CMSXS116R[a] | SC326-6; BR005R | 27 ± 5.6 a | 24 ± 0.6 a | 12 ± 1.7 a |
| CMSXS180R[a] | | 22 ± 0.1 a | — | — |
| IS10562 | CMSXS230B | 23 ± 1.4 a | — | — |
| Tx631B[a] | CMSXS205B | 25 ± 2.0 a | — | — |
| CMSXS225R[a] | | 103 ± 5.1 d | 88 ± 5.3 c | 32 ± 1.4 a |
| QI3 | | 16 ± 1.5 a | — | — |
| SC566-14[a] | | 132 ± 2.1 e | 134 ± 4.9 d | 65 ± 10.4 c |
| 9910032 | | 33 ± 4.9 b | — | — |
| Tx430 | CMSXS110R | 20 ± 0.4 a | — | — |

Values are the means of three replications for the Al activity of {27} μM $Al^{3+}$ and two replications for the other Al activities. Seven plants per replication were used for all Al treatments. Accessions whose RNRG means are followed by the same lower-case letters within each of the 3 Al activities constitute homogeneous RNRG groups by the Scott-Knott test (P < 0.05). (Caniato et al., supra).

Example 2

DNA Isolation and Marker Analysis

Genomic DNA was isolated from approximately 500 mg of leaf tissue from inbred lines and $F_2$ individuals for each segregating population using the protocol described by Saghai-Maroof et al. (1984. *Proc. Natl. Acad. Sci. USA* 81:8014-8018). As part of a positional cloning effort to isolate the SbMATE gene, genotyping of the two sequenced-tagged site (STS) markers designated CTG29 (CTG29F: 5'-HEX-STG-CAGTATCT GCAGTATCATTT; SEQ ID NO:9) and CTG29R: AATCCGTCAGGTCAGCAATC; SEQ ID NO:10) and M181 (M181F: 5'-6FAM-AAGGCAACAACT-GAGGCACT; SEQ ID NO:11), M181R: TCGCTA-GAGTGGTGCAAGAA; SEQ ID NO:12), which flanked the Al tolerant gene were carried out as described in Caniato et al., supra. Genetic distances in the RIL population were determined from recombination frequencies using the Kosambi function (Kosambi, supra) with a LOD=3 and a maximum recombination frequency of θ=0.4.

FIG. 1a shows the RIL map of $Alt_{SB}$ that included the two STS markers, CTG29 and M181, located at 0.8 cM and completely linked to $Alt_{SB}$, respectively. Our final stage of genetic mapping for the $Alt_{SB}$ region involved screening 4170 gametes from an $F_2$ population and selecting 27 recombinant individuals from the CTG29-M181 interval. Upon progeny testing of derived $F_{2:3}$ families, 6 individuals showed recombination events between $Alt_{SB}$ and M181, indicating that CTG29 and M181 flanked the $Alt_{SB}$ locus. The STS marker T755 at the leftmost end of sorghum BAC 55D12 was completely linked to $Alt_{SB}$ in all recombinants; thus, BAC181g10, which spanned T755, was selected for shotgun sequencing. Because only M181 was located on 181g10, whereas CTG29 was located on a sorghum BAC physically unlinked to the contig shown in FIG. 1a, a G/A SNP next to open reading frame (ORF) 2 within 181g10 (FIG. 1b) was placed onto the high resolution map to confirm that 181g10 contained $Alt_{SB}$. Within the 21 single recombinants originally detected between the more distant CTG29 and $Alt_{SB}$, the G/A SNP identified only 4 recombinants, indicating that ORF2 was significantly closer to $Alt_{SB}$ than CTG29 and confirming that our chosen BAC spanned the $Alt_{SB}$ locus. Additional markers were developed from our sequence analysis of BAC 181g10 and used to further delimit the $Alt_{SB}$-containing interval. Two of these markers each identified a single recombination event, thus closely flanking $Alt_{SB}$. Therefore, an average recombination ratio of ~513 Kb/cm across this region allowed us to define a 24.6 Kb region that contained three predicted ORFs (ORF 7, 8, and 9), one of which had to be $Alt_{SB}$ (FIG. 1b).

Example 3

Isolation and Structure of the Full Length cDNA for SbMATE

The 5' and 3' end sequences of SbMATE transcripts were identified by 5'/3'-rapid amplification of cDNA (RACE) using a GeneRacer kit (Invitrogen) according to the manufacturer's instructions. First-strand cDNA was reverse transcribed from 1 μg of total RNA from roots of the Al-tolerant NIL (ATF10B) with the GeneRacer oligo dT primer (5'-GCTGTCAAC-GATACGCTACGTAACGGCATGACAGTG(T)$_{24}$-3'; SEQ ID NO: 13). The PCR of 5'-cDNA ends was carried out with the GeneRacer kit using a 5' primer specific to the adaptor ligated to cDNA ends (5'-CGACTGGAGCACGAGGACAC TGA-3'; SEQ ID NO:14) and JL56 (5'-ATACCGAG-GAAGCGCCGGAAT-3'; SEQ ID NO:15), a gene-specific primer (GSP) corresponding to the SbMATE cDNA. Nested PCR was carried out with GeneRacer 5' nested primer (5'-GGACACTGACATGGACTG AAGGAGGTA-3'; SEQ ID NO:16) and JL54 (5'-CCTTGAACCCACGGAAGACT-3'; SEQ ID NO:17), the nested GSP. The PCR of 3'-cDNA ends was carried out with the GeneRacer kit using a 3' primer specific to the oligo dT primer ligated to 3'-cDNA ends (5'-GCTGTCAACGATACGCTACGTAACG-3'; SEQ ID NO:18) and JL55 (5'GCCCGCGCTGCGCTACCTGA-3'; SEQ ID NO:19), a GSP. Nested PCR was carried out with GeneRacer 3'Nested primer (5'-CGCTACGTAACGGCAT-GACAGTG-3'; SEQ ID NO:20) and JL48 (5'-ACGCT-GATAATGCTGAGCAAGCTG-3'; SEQ ID NO:21), a nested GSP. Cycling parameters used in this 3'/5'-RACE protocol were 34 cycles at 94° C. for 30 s, at 58° C. for 40 s and 72° C. for 1 min. The PCR products were subcloned into a pCR4-TOPO vector (Invitrogen, Carlsbad, Calif.) and sequenced with a DNA sequencer. According to the 5'- and 3'-end sequences, the full-length cDNA of SbMATE was amplified with PCR primers JL96 (5'-GTACGATCGACACGAGM-CTG TACGTA-3'; SEQ ID NO:22) and JL97 (5'-TGCTTGC-MGGTTTGTAGCTAGGCCGA-3'; SEQ ID NO:23). The PCR products were subcloned into a pCR4-TOPO vector and sequenced.

Sequence annotation for ORFs 8 and 9 revealed high similarity to a hypothetical protein and a sucrose phosphate synthase gene, respectively. FIG. 1c shows that both genes were highly expressed in shoots of near-isogenic lines (NILs) contrasting in Al tolerance but were not expressed in roots, the site where the Al tolerance mechanism must function. Conversely, Conversely, TBLASTX searches with ORF 7 identified highly similar sequences in *Arabidopsis* (At1g51340; SEQ ID NO:24) and rice (Os01g69010; SEQ ID NO:25) (FIG. 2a), which represent members of the multidrug and toxic compound extrusion (MATE) transporter family (Brown et al. 1999. *Mol. Biol.* 31: 393-395). MATE proteins have been implicated in the efflux of small organic molecules (Morita et al. 1998. *Antimicrob. Agents Chemother.* 42: 1778-1782; Diener et al. 2001. *Plant Cell* 13: 1625-1638; Li et al. 2002. *J. Biol. Chem.* 277: 5360-5368), which is consistent with the physiological mechanism for sorghum Al tolerance based on Al-activated root citrate exudation (Magalhaes et al., supra). Therefore, the MATE homolog isolated from *Sorghum bicolor* (here designated SbMATE) was considered the best candidate for $Alt_{SB}$ and studied further.

The genomic SbMATE in sorghum is 2407 bp long. The genomic sequence for the SbMATE from the Al tolerant parent (SC283) is identified by SEQ ID NO:1 and the genomic sequence for the SbMATE from the Al sensitive parent (BR007), by SEQ ID NO:2 The full length cDNA (SEQ ID NO:3) contains 5 exons distributed over 1803 bp (FIG. 2c), which encode a 600-amino acid polypeptide (SEQ ID NO:4) with a molecular weight of ~62 kD. Sequence comparisons with the wheat Al tolerance gene, ALMT1, showed that the sorghum SbMATE is not related to the ALMT family of membrane proteins and thus is a novel tolerance gene. The topology program HMMTOP (Tusnady and Simon. 1998. *J. Mol. Biol.* 283: 489-506) predicted the SbMATE protein to contain 12 transmembrane domains (FIG. 2b) and is suggested to be localized to the plasma membrane (PSORT; Nakai and Kanehisa. 1992. *Genomics* 14: 897-911). A comparison between the SC283 (Al tolerant) and BR007 (Al sensitive) SbMATE alleles as well as for the entire 24.6 Kb region defined by high resolution mapping, showed that the SbMATE coding region is identical between the parental alleles, with polymorphisms only found within one of the introns (FIG. 1d). There were only 4 sets of polymorphisms found in the entire 24.6 Kb region with the most divergent being a large, 728 bp indel in the SbMATE promoter region at ~1.4 Kb upstream of the predicted TATA box.

Example 4

Determination of Gene Expression Via Semi-Quantitative Reverse Transcription PCR Sorghum seedlings were grown as described above and in Caniato et al., supra in nutrient solution with {27} μM $Al^{3+}$ or without Al (control solution) for 3 days. Each experimental unit consisted of 10 root apices (1 cm) and 3 replications were used for each treatment. Root apices were collected, frozen in liquid nitrogen, and total RNA was extracted using the RNeasy Plant Mini Kit (Qiagen, Valencia, Calif.). First strand cDNA was synthesized using 300 ng of DNase I-treated RNA, 500 ng of anchored oligo(dT) 12-18 mers and 100 μmoles of each dNTP in a total volume of 12 μL. Samples were heated at 65° C. for 5 min and transferred to ice. Subsequently, 4 μL of 5× reaction buffer (Invitrogen, Carlsbad, Calif.), 2 μL DTT 0.1M and 1 μL DEPC water were added to the mix. The mix was incubated at 42° C. for 2 min followed by the addition of 1 μL of SuperScript II RT (Invitrogen) and final incubation at 42° C. for 90 min. first strand cDNA samples were then subjected to 70° C. for 15 min and stored at −20° C. A 800 bp cDNA fragment, spanning the $3^{rd}$ to $5^{th}$ exons of the SbMATE transcript, was amplified from the $1^{st}$ strand cDNA samples using the primers JL57 (5'-GTGCTG-GAT CCGATCCTGAT-3'; SEQ ID NO:26) and JL58 (5'-CACTGCCGAAGAAACTTCCA-3'; SEQ ID NO:27). A ~500 bp fragment of the Actin gene amplified with primers ActF (5'-TGATGAAGATTCTCACTGAG-3'; SEQ ID NO:28) and ActR (5'-GATCCACMTCTGTT GGMCG-3'; SEQ ID NO:29), was used as an internal control. PCR reactions were run with 2 μL of the cDNA mix; 20 mM Tris-HCl (pH 8.4); 50 mM KCl; 2 mM $MgCl_2$; 0.125 mM dNTP; 10 pmoles of each primer and 0.5 U of Taq DNA polymerase (Invitrogen) in a 20 μL reaction volume. PCR reactions were undertaken with an initial denaturation step at 94° C. for 1 min followed by 30 cycles at 94° C. for 30 s, at 60° C. for 40 s and 72° C. for 90 s, with a final step at 72° C. for 5 min. The PCR reactions for SbMATE and the Actin gene were found to be in the linear phase at 30 PCR cycles, which was the number of cycles chosen for the semi-quantitative RT-PCR assays.

Quantitative RT-PCR analysis showed that SbMATE is expressed only in roots of the Al-tolerant NIL (FIG. 3a) and that the root tip expression is Al-inducible (FIG. 3c); expression is not detectable in the root tip of the sensitive NIL. Sorghum Al tolerance is also Al-inducible over time (FIG. 3b, left panel).

SbMATE expression was also examined in a 12 member sorghum diversity panel from diverse geographical origins and included BR007, the Al sensitive parent and SC283, the Al tolerant parent. The wide range of Al tolerance and sensitivity exhibited by this panel is due to an allelic series at the $Alt_{SB}$ locus (Caniato et al., supra). Differences in SbMATE expression explained most, i.e., 96%, of the phenotypic variation for Al tolerance in this panel ($r^2$=0.96, FIG. 4a). These results provide further evidence that SbMATE underlies $Alt_{SB}$ and strongly suggests that differences in gene expression constitute the basis for allelic variation at $Alt_{SB}$. Significant correlation was similarly found between SbMATE expression and Al-activated root tip citrate release (FIG. 4b), and between citrate release and Al tolerance (FIG. 4c), indicating that differences in gene expression condition the Al tolerance phenotype primarily by modulating root citrate exudation.

The large polymorphic region upstream of the SbMATE start codon (see FIG. 1d) was amplified via PCR in an expanded sorghum panel and the size variation for this polymorphic region was found to be significantly and positively correlated with Al tolerance (FIG. 4d). This variable region was sequenced from genotypes representing the four size classes for this region (FIG. 4d) and analysis of the sequence data indicated this region was highly structured and repeated. As shown in FIG. 4e, this region is composed of an initial 100 bp sorghum sequence (unit a in FIG. 4e), followed by a larger, 243 bp sequence (unit b), that is a Tourist-like miniature inverted repeat transposable element or MITE (Bureau and Wessler, 1992 Plant Cell 4: 1283-1294; Wessler et al. 1995. Curr. Opin. Genet. Dev. 5: 814-821). The MITE insert is followed by a subsequent 21 bp sorghum sequence (unit c). This a-b-c structure is a singlet in the smallest, least Al tolerant example (Tx430) and is repeated between 3, 4, and 5 times in representatives from the next three size classes. The DNA sequence for this region in the representative sorghum lines for the 4 size classes is shown in FIG. 5.

Example 5

Determination of Gene Expression Via Quantitative Real-Time Reverse Transcription PCR Sorghum seedlings were grown as described above and in Caniato et al., supra in nutrient solution with {27} μM $Al^{3+}$ or without Al (control solution). Root and shoot tissues were collected 1, 3, and 6 days after +/−Al treatment. Three replications were employed for each treatment.

Total RNA was extracted from individual tissue samples using the RNeasy Plant Mini Kit (Qiagen, Valencia, Calif.). First-strand cDNA was synthesized using 7.5 μg of total RNA using the High-Capacity Archive Kit (Applied Biosystem).

SbMATE transcripts were quantified using the ABI Prism 7900 Sequence Detection System (Applied Biosystems). A series of cDNA dilutions were used for making standard curves both for SbMATE transcripts and for 18S RNA which was used as the internal reference. Then, the selected dilution for specific cDNA samples (100 ng for SbMATE transcripts, 1 ng for 18S RNA) were used as real-time PCR templates to quantify relative transcript levels using the conditions recommended by the manufacturer. The forward and reverse primers, as well as the probe specific to SbMATE, are ORF7-F (5'-CAGCCATTGCCCATGTTCTTT-3'; SEQ ID NO:30), ORF7-R (5'-ACCAGCTTGCTCAGCATTATCA-3'; SEQ ID NO:31) and Probe (6FAM-CCCAGTACCTGATAACGC-TRMRA; zSEQ ID NO:32), respectively. Levels of endogenous 18S RNAs were determined using Taqman Ribosomal RNA Control Reagents (Applied Biosystems). Distilled water or products of room temperature reactions without reverse transcriptase were used as negative controls. The levels of the SbMATE transcripts were normalized to endogenous 18S RNA. Each set of experiments was replicated three times.

As seen in the left panel of FIG. 3b, Sorghum Al tolerance is also Al-inducible over time. Al-induced inhibition of root growth decreases significantly in the tolerant NIL as root exposure time to Al increases, with inhibition of root growth decreasing from an initial inhibition of 40-50% observed on days 1 and 2 in the presence of Al, to no inhibition of root growth on days 5 and 6. This response correlates closely with the increase in Al-activated root tip citrate exudation over time of exposure to Al (FIG. 3b; right panel) and Al-induction of SbMATE expression (FIG. 3c). Exposure to Al increased SbMATE expression by 20% after one day in Al; Al inducibility increased to 40% by day 3 in Al, and by 120% by day 6. Altogether, the parallel behavior between SbMATE expression, Al tolerance and root citrate release supports our contention that the transporter is the Al tolerance locus, $Alt_{SB}$.

Example 6

Confirmation of the Identity of the SbMATE Gene by Phenotypic Complementation WT Col and AtALMT1-KO A genetic complementation test was carried out in the Arabidopsis thaliana ecotype Columbia (WT Col) and in the highly Al sensitive T-DNA knockout mutant, AtALMT1-KO, in which an Arabidopsis homolog of the wheat ALMT1 gene is disrupted in the first exon. We screened 10 T-DNA Arabidopsis insertion lines in which the 6 Arabidopsis genes that are the most closely related to SbMATE homologs were disrupted, and observed no reduction of Al tolerance in comparison to the Col-0 WT. This indicates that functional MATE alleles are either rare in Arabidopsis or not present in the Columbia ecotype. Conversely, the disruption of AtALMT1 caused a strong reduction in Al tolerance compared to WT (FIG. 6a), as the result of a lack of AtALMT1 function that leads to a nearly complete loss of Al-activated root malate efflux (Hoekenga et al., supra). Therefore, we conclude that the extremely Al sensitive AtALMT1-KO is a highly appropriate genetic background for Al tolerance complementation tests in Arabidopsis. Homozygous T3 lines expressing SbMATE driven by the CaMV 35S promoter were significantly more Al tolerant than control seedlings in both backgrounds (FIG. 6a). Four transgenic lines in the WT background (TG-WT) significantly outperformed the WT Columbia with regard to Al tolerance, with an average RNRG of 88±4% compared to a RNRG of 65±5% for the WT line. Expression of SbMATE in the highly Al sensitive AtALMT1 background increased the sensitivity of the complementation test, as eight transgenic lines in the KO background (TG-KO) exhibited a significant increase in Al tolerance compared to the parental line (FIG. 6b). In a separate experiment, we selected the best performing as well as a mediocre performing transgenic line in both backgrounds and found that Al tolerance increased proportionally with the level of SbMATE expression (FIG. 6c). The most tolerant transgenic lines in both backgrounds, Col-TG4 and K0-TG8, exhibited the greatest SbMATE expression and Al-activated root citrate release, but no increase in malate exudation was observed (FIG. 6d). We are generating transgenic wheat lines in the Al-sensitive cultivar, Bobwhite, where SbMATE driven by the maize ubiquitin promoter is stably expressed. In FIG. 7, the results of an experiment with T1 transgenic wheat lines shows that we have identified four transgenic lines with substantially increased Al tolerance compared to non-transgenic Bobwhite. These results with *Arabidopsis* and wheat provide experimental support that a member of the MATE family from *Sorghum bicolor*, SbMATE, is an Al-activated citrate efflux transporter that confers Al tolerance via the $Alt_{SB}$ locus.

Example 7

Subcellular Localization of SbMATE

The membrane localization of SbMATE was determined by examining the transient expression of the SbMATE coding region tagged with GFP in onion (*Allium cepa*) epidermal cells. 35S::$Alt_{SB}$:GFP constructs were generated by amplification of the SbMATE coding region using adaptor primers that incorporated SpeI restriction site linkers for sub-cloning into the plant transformation vector, pCAMBIA 1302. The latter contains a CaMV 35S promoter driving the expression of an mGFP5 gene. Insertion of SbMATE between the CaMV 35S promoter and the GFP coding region of the opened pCAMBIA vector generated the translational in-frame fusion of the SbMATE::GFP chimera driven by the CaMV 35S promoter. The resulting construct was fully sequenced and checked for sequence accuracy. Transient expression of the SbMATE::GFP chimera was achieved by particle bombardment of epidermal onion cells. Briefly, M10 tungsten particles (1.1 μm) were coated with one microgram of the SbMATE::GFP (or empty pCAMBIA 1302 vector as a negative control) plasmid DNA in 2.5 M $CaCl_2$ and 1M spermidine (Sigma, USA). Epidermal onion peels were bombarded at a helium pressure of 27 MPa (rupture disks 1300 p.s.i.; Biolistic PDS-2000/He BioRad Laboratories, Hercules, Calif.) with the DNA-coated particles, and the tissue was incubated on filter paper immersed in tap water in the dark at room temperature for 24 hr. Imaging of GFP fluorescence was carried out using confocal microscopy (Leica TCS SP2 system, Leica, Germany).

The subcellular localization of SbMATE was determined via transient expression of a SbMATE::GFP translational fusion protein in onion epidermal cells (See Example 7). The SbMATE protein appears to be localized to the plasma membrane (FIG. 3d), which is consistent with its proposed role in citrate efflux from root cells. Thus, these findings indicate that our candidate MATE gene for the $Alt_{SB}$ locus encodes a root citrate efflux transporter that is Al-inducible at the level of gene transcription and is also Al-activated at the level of protein function.

Example 8

Determination of Al-Activated Root Citrate Exudation in Sorghum Near-Isogenic Lines Seeds for the Al-tolerant (ATF 10B) and Al-sensitive (ATF8B) near-isogenic lines (NILs) were surface-sterilized with 0.5 (w/v) NaOCl for 15 min, rinsed with ultrapure water and allowed to germinate for 3 days at 26° C. Seedlings were then transplanted to 8 L tubs containing complete nutrient solution lacking Al (Magnavaca et al., supra) at pH 4.0. After 24 hr the solution was changed to either control nutrient solution (—Al) or nutrient solution containing {27} μM $Al^{3+}$ and root exudates were collected after 1, 3, and 6 days of treatment with {0} or {27} μM $Al^{3+}$. Six seedlings were used for each determination of organic acids in the root exudates; root exudate collection began by transferring the six seedlings to a 50 ml plastic centrifuge tube containing 4.3 mM $CaCl_2.6H_2O$ with or without Al added as $AlCl_3.6H_2O$ with the same free $Al^{3+}$ activity of {27} μM $Al^{3+}$ (pH 4.5) as was used when seedlings were grown in the Magnavaca nutrient solution prior to collection of root exudates. Each root exudate determination was replicated four times. Root exudates were collected for 6 hr, and then the exudate solution was passed through anionic and cationic chromatography columns to remove Al and inorganic anions that interfere with the determination of organic acids. Subsequently, 1 mL subsamples were lyophilized and resuspended in 0.2 mL of ultrapure water. Analysis of organic acids in root exudates was performed using a capillary electrophoresis system as described in Pineros et al. (2002. *Plant Physiol.* 129: 1194-1206).

Example 9

SbMATE Orthologs in Divergent Plant Species

Possible homologs of the sorghum SbMATE in maize were identified using recursive searches. Sorghum SbMATE was used to query the rice genome using TBLASTN at Gramene and seven putative homologs to SbMATE were identified. The maize MAGI GSS database was then queried with the sorghum SbMATE and also with sequences from the seven rice SbMATE-like genes. The maize MATE with the closest sequence similarity to or sorghum MATE, designated ZmASL49968 (for *Zea mays* $Alt_{SB}$-like gene) was chosen for further analysis. This gene shared 64% identity and 73% similarity with the sorghum SbMATE gene at the amino acid level. Two lines of investigation are utilized to identify genes and processes important for Al tolerance. The first, utilizing association analysis, a statistical genetic approach, to correlate particular nucleotide polymorphisms with significant differences in Al tolerance between inbred lines. This analysis is subsequently followed by linkage analysis in selected F2 populations in order to further verify associations found with Al tolerance. Three datasets are required for association analysis: 1) trait data, 2) genotype data, and 3) sufficient marker data from across the genome of the study population, in order to evaluate true positive from false positive results (those due to population structure or kinship). We have phenotyped the 288 inbred line association panel assembled Dr. Ed Buckler, USDA-ARS, Cornell University, using our standard hydroponic methodologies for quantifying root growth under +/−Al conditions. Based on five repeated experiments, the estimate for the heritability of net seminal root growth (the amount of root growth that occurs during a 2-day stress treatment) is 0.65. We are using the latest form of mixed model ANOVA; this model was developed by Dr. Ed Buckler and colleagues and has been recently published in *Nature Genetics* (2006. 38:203-208). We are employing a set of 500 SNP from across the maize genome to empirically calculate the significance threshold for Al tolerance.

We then sequenced the region of ZmASL-49968 depicted in FIG. 8a in all 288 of the inbred lines in the maize association panel. Statistical analysis indicates that polymorphisms in this gene are significantly associated with maize Al tolerance, strongly suggesting this is a candidate Al tolerance gene. The details of the association analysis for this gene are depicted in FIG. 8b. The significance of this gene in maize Al tolerance was then verified with a linkage population, using an F2 cross between parents known to differ in the alleles detected for ZMASL-49968 (B73×CML247). As seen in FIG. 9, the superior allele of ZmASL-49968 carried by the B73 variety is completely dominant to the sensitive allele carried by CML247.

Microarray analysis was used to examine global gene expression profiling in the maize root tip of Al tolerant and sensitive maize genotypes. We identified a second candidate maize Al tolerance gene as a homolog of SbMATE in sorghum. As seen in FIG. 10, we found three genes in the maize root tip whose expression were strongly induced by Al only in the root tip of the tolerant maize lien and also showed higher constitutive (—Al) expression in the tolerant line. One of these, MZ000025698 in FIG. 10, was derived from EST NP667103 and is closest in sequence to the sorghum SbMATE for the 3 Al-inducible MATE genes in maize (53% identical at the amino acid level) and was chosen for further study. Markers were derived for a region of this gene and mapped on the Embrapa Recombinant Inbred line population derived from the cross between an Al tolerant×sensitive parent. As seen in FIG. 11, this gene maps to a major Al tolerance QTL previously identified by Embrapa Maize and Sorghum using this population. Finally, we confirmed the microarray results with RT-PCR analysis of expression of this gene in the root tips of two Al tolerant maize lines, Al237 and Cat100-6 and the Al sensitive line, L53. Al237 and L53 are the parents of the Embrapa RIL mapping population. As seen in FIG. 12, the gene is expressed much more strongly in the root tips of the 2 tolerant lines, both in the absence and presence of Al.

The results with *Arabidopsis* and wheat discussed above provide experimental support that a member of the MATE family from *Sorghum bicolor*, SbMATE, is an Al-activated citrate efflux transporter that confers Al tolerance via the $Alt_{SB}$ locus.

Figure 2:
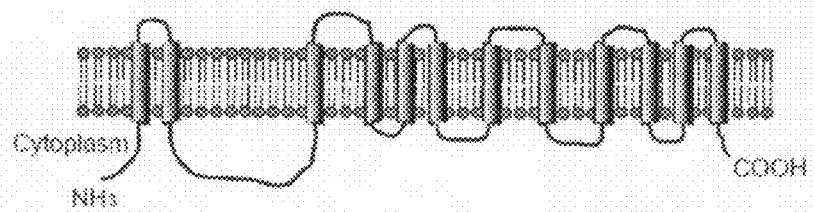
FIGS. 2a-c show (FIG. 2a) the amino acid sequence alignments for sorghum SbMATE (SEQ ID NO:4) and homologs from Arabidopsis [At1g51340 (SEQ ID NO:24), percent amino-acid identity (I)=51%; expected value (E)=1.1e$^{-121}$] and rice (Os01g69010 (SEQ ID NO:25), I=63%; E=1.1e$^{-152}$), the structure of the SbMATE protein showing predicted transmembrane domains and hydrophilic loops linking specific transmembrane domains (FIG. 2b), and the intron-exon structure of the SbMATE gene (FIG. 2c).
Figure 2:

In addition, orthologs with a high degree of sequence identity were found in other plants including *Arabidopsis* and rice (FIG. 2).

Example 10

Expression of Sorghum SbMATE in Transgenic *Arabidopsis* Seedlings and Analysis of *Arabidopsis* Al Tolerance and Root Organic Acid Exudation An SbMATE cDNA fragment spanning from the start codon to the termination codon of $Alt_{SB}$ was amplified by PCR with the primers JL115 (5'-AATATCTAGACGATC GACACGAGACTGTACGT-3'; SEQ ID NO:33; underlined bases denote the XbaI site) and JL116 (5'-AATA CCCGGGAAGGTTTGTAGCTAGGCCGA-3'; SEQ ID NO:34; underlined bases denote the XmaI site) from the Al-tolerant NIL, ATF10B. Restriction-digested PCR products were cloned into the pBAR2 vector between the corresponding restriction sites, which are located after the CaMV 35S promoter.

Both the empty vector and the vector plus SbMATE were individually electroporated into the *Agrobacterium tumefaciens* strain GV3101 (Invitrogen) and used for *Arabidopsis thaliana* transformation (in both the Columbia-0 and AtALMT knockout backgrounds). The presence of the transgene was confirmed by Basta herbicide resistance of the transgenic plants and by PCR confirmation of T-DNA insertions.

About 60 independent T2 lines transformed with the 35S::SbMATE construct were tested for root growth in hydroponic solution as described by Hoekenga et al., supra. Three T2 lines transformed with the empty vector in each of the wild-type (Col-0) and AtALMT knockout backgrounds were also included as controls for the root growth experiments.

Individual T2 lines with enhanced root growth rate in the presence of Al indicating increased Al tolerance as compared to corresponding controls were selfed and the segregating T3 progeny analyzed to identify transgenic and non-transgenic homozygous T3 progenies, which were confirmed by progeny testing. Corresponding transgenic and non-transgenic homozygous T3 lines were then paired and used for determination of Al tolerance (root growth) as described in Hoekenga et al., supra.

For determination of root organic acid exudation, ~2-3 mg of surface sterilized and stratified seeds for each *Arabidopsis* transgenic and non-transgenic line were germinated in Magenta boxes containing sterile hydroponic growth solution for six days (see Hoekenga et al., supra, for details). Subsequently, seedlings of individual transgenic lines were transferred to 20 mL of the filter-sterilized exudation solution (pH 4.2) with or without a total Al concentration of 13.6 µM $AlCl_3$ ($Al^{3+}$ activity of 1.5 µM) in a sterile Petri dish for 2 days. The exudation solutions were collected at the end of the second day of treatment, and passed through anionic and cationic chromatography columns to remove $Al^{3+}$ and inorganic anions that interfere with the determination of organic acid anions. Subsequently, 1 mL sub-samples were analyzed for organic acids in the root exudate using the capillary electrophoresis system as described in Pineros et al., supra.

Homozygous T3 lines expressing SbMATE driven by the CaMV 35S promoter were significantly more Al tolerant than control seedlings in both backgrounds (FIG. 6a). Four transgenic lines in the WT background (TG-WT) significantly outperformed the WT Columbia with regard to Al tolerance, with an average RNRG of 88±4% compared to a RNRG of 65±5% for the WT line. Expression of SbMATE in the highly Al sensitive AtALMT1 background increased the sensitivity of the complementation test, as eight transgenic lines in the KO background (TG-KO) exhibited a significant increase in Al tolerance compared to the parental line (FIG. 6b). In a separate experiment, we selected the best performing as well as a mediocre performing transgenic line in both backgrounds and found that Al tolerance increased proportionally with the level of SbMATE expression (FIG. 6c). The most tolerant transgenic lines in both backgrounds, Col-TG4 and K0-TG8, exhibited the greatest SbMATE expression and Al-activated root citrate release, but no increase in malate exudation was observed (FIG. 6d). The successful phenotypic complementation of SbMATE in the *Arabidopsis* mutant provides strong evidence that SbMATE can work across species to enhance Al tolerance.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A method of producing a genetically transformed plant wherein the method comprises:
   (a) cloning or synthesizing a nucleic acid molecule encoding a Al-inducible citrate efflux transporter polypeptide, wherein said nucleic acid molecule is selected from the group consisting of: (i) the nucleic acid molecule shown in SEQ ID NO:1; (ii) a nucleic acid molecule encoding SEQ ID NO:4; and (iii) a nucleic acid molecule encoding an amino acid sequence at least 95% identical to the amino acid sequence shown in SEQ ID NO:4, wherein said nucleic acid molecule encodes a polypeptide capable of providing tolerance to aluminum to a plant;
   (b) inserting the nucleic acid molecule in a vector so that the nucleic acid molecule is operably linked to a promoter;
   (c) insert the vector into a plant cell or plant seed;
   (d) expressing said nucleic acid molecule in said plant cell or seed; and
   (e) regenerating a plant from the plant cell or plant seed, wherein tolerance to aluminum in the plant is increased compared to a wild type plant.

2. An isolated or recombinant DNA molecule comprising a nucleotide sequence encoding a polypeptide having the amino acid sequence as set forth in SEQ ID NO:4 or the full complement of said nucleotide sequence.

3. The isolated or recombinant DNA molecule of claim 2 further comprising a second nucleotide sequence encoding a regulatory element wherein said element is a constitutive promoter, operatively linked so that the promoter enhances transcription of the nucleotide sequence encoding the polypeptide having the amino acid sequence set forth in SEQ ID NO:4 in root tissue in response to the presence of aluminum $Al^{3+}$.

4. The isolated or recombinant DNA molecule of claim 2 further comprising a second nucleotide sequence encoding a regulatory element wherein said element is a tissue-specific and aluminum-inducible promoter, operatively linked so that the promoter enhances transcription of the nucleotide sequence encoding the polypeptide having the amino acid sequence set forth in SEQ ID NO:4 in root tissue in response to the presence of aluminum Al$^{+3}$.

5. The isolated DNA molecule of claim 2 further comprising a polymorphic nucleotide sequence as set forth in SEQ ID NO: 5.

6. The isolated or recombinant DNA molecule according to any one of claims 2-5 wherein said nucleotide sequence is the genomic nucleotide sequence as set forth in SEQ ID NO:1.

7. The isolated or recombinant DNA molecule according to any one of claims 2-5 wherein said nucleotide sequence is cDNA.

8. The isolated or recombinant DNA molecule according to claim 2 wherein said nucleotide sequence is cDNA having the sequence as set forth in SEQ ID NO:3.

9. An isolated or recombinant nucleic acid molecule comprising a nucleotide sequence selected from the group consisting of:
(a) a nucleotide sequence having at least 95% sequence identity to a nucleotide sequence that encodes SEQ ID NO:4 wherein said nucleotide sequence encodes a polypeptide having aluminum-inducible citrate efflux transporter activity resulting in tolerance to Al$^{3+}$ in plant cells; and
(b) a nucleotide sequence that comprises the full complement of (a).

10. A recombinant construct comprising (i)the DNA molecule of claim 2 wherein said DNA is cDNA and (ii) one or more regulatory elements operatively linked to said nucleotide sequence wherein aluminum-induced expression of said cDNA results in production of an aluminum-inducible citrate efflux transporter polypeptide, SbMATE (*Sorghum bicolor* Multidrug and Toxin Efflux) which imparts tolerance to Al$^{3+}$ in plant cells.

11. The recombinant construct of claim 10 wherein said regulatory element is a constitutive, inducible, or tissue-specific promoter operably linked to said nucleotide sequence.

12. The recombinant construct of claim 10 wherein said regulatory element is the CaMV 35S promoter.

13. A recombinant construct comprising the DNA molecule of claim 4 wherein said DNA is cDNA and wherein aluminum-induced expression of said cDNA is specifically expressed in plant root cells and results in production of an aluminum-inducible citrate efflux transporter polypeptide, SbMATE(*Sorghum bicolor* Multidrug and Toxin Efflux), in the plant root cells resulting in tolerance to Al$^{3+}$ in said plant root cells.

14. A recombinant construct comprising the DNA molecule of claim 5 wherein said DNA is cDNA and wherein aluminum-induced expression of said cDNA is specifically expressed in roots and results in production of an aluminum-inducible citrate efflux transporter polypeptide as set forth in SEQ ID NO:4.

15. A vector comprising the recombinant DNA molecule of claim 2.

16. A host cell comprising the vector of claim 15.

17. The host cell of claim 16, wherein said host cell is a single-celled or multi-celled organism into which the construct is introduced.

18. The host cell of claim 16, wherein said host cell is a plant cell.

19. The host cell of claim 18, wherein the plant cell is from a plant selected from the group consisting of *Arabidopsis*, wheat, maize, sorghum, or rice.

20. A transgenic plant in which the cDNA according to claim 10 has been introduced or a progeny of said plant, wherein said progeny also contains the cDNA and wherein expression of said cDNA in said plant and progeny of , said plant results in production of an aluminum-inducible citrate efflux transporter polypeptide resulting in Al-induced tolerance to Al$^{3+}$ in said plant and progeny of said plant.

21. The transgenic plant of claim 20 wherein expression of said cDNA in said plant and progeny of said plant results in increase of citrate exudation which facilitates the ability of said plant to acquire phosphorous from acid soil.

22. A plant cell, a plant part, or a plant tissue of the plant of claim 20, wherein said plant cell, plant part or plant tissue comprises the cDNA.

23. The plant part of claim 22 wherein said plant part is a root.

24. A transgenic seed of the transgenic plant according to claim 20, wherein said seed comprises the cDNA.

25. A transgenic plant comprising plant cells containing the recombinant construct of claim 14.

26. A plant part from the transgenic plant according to claim 25, wherein the plant part contains the recombinant construct.

27. A transgenic seed of the transgenic plant according to claim 26.

28. The seed of claim 27, wherein the seed is true breeding for an increased tolerance to aluminum as compared to a wild type variety of the seed.

29. A transgenic plant produced according to a method wherein the method comprises:
(a) cloning or synthesizing a nucleic acid molecule encoding a Al-inducible citrate efflux transporter polypeptide, wherein said nucleic acid molecule is selected from the group consisting of: (i) the nucleic acid molecule shown in SEQ ID NO:1; (ii) a nucleic acid molecule encoding SEQ ID NO:4; and (iii) a nucleic acid molecule encoding an amino acid sequence at least 95% identical to the amino acid sequence shown in SEQ ID NO:4, wherein said nucleic acid molecule encodes a polypeptide capable of providing tolerance to aluminum to a plant;
(b) inserting the nucleic acid molecule in a vector so that the nucleic acid molecule is operably linked to a promoter;
(c) insert the vector into a plant cell or plant seed;
(d) expressing said nucleic acid molecule in said plant cell or seed; and
(e) regenerating a plant from the plant cell or plant seed, wherein tolerance to aluminum in the plant is increased compared to a wild type plant.

* * * * *